(12) United States Patent
Nakagawa et al.

(10) Patent No.: US 7,197,529 B2
(45) Date of Patent: Mar. 27, 2007

(54) NETWORK SYSTEM FOR RADIOGRAPHING RADIATION-IMAGES

(75) Inventors: Masayuki Nakagawa, Tokyo (JP); Wataru Motoki, Tokyo (JP)

(73) Assignee: Konica Corporation, Tokyo (JP)

(*) Notice: Subject to any disclaimer, the term of this patent is extended or adjusted under 35 U.S.C. 154(b) by 741 days.

(21) Appl. No.: 10/108,158

(22) Filed: Mar. 27, 2002

(65) Prior Publication Data

US 2002/0152287 A1 Oct. 17, 2002

(30) Foreign Application Priority Data

Apr. 17, 2001 (JP) ............................. 2001-118143

(51) Int. Cl.
*G06F 15/16* (2006.01)
(52) U.S. Cl. ..................... 709/200; 378/29; 378/167; 382/132
(58) Field of Classification Search ................ 709/204, 709/203, 200–202, 217–227; 378/162, 98, 378/98.8, 28–29, 167, 169; 382/128–132
See application file for complete search history.

(56) References Cited

U.S. PATENT DOCUMENTS

| | | | | |
|---|---|---|---|---|
| 5,235,510 A | * | 8/1993 | Yamada et al. | 600/300 |
| 5,334,851 A | * | 8/1994 | Good et al. | 250/582 |
| 5,522,067 A | * | 5/1996 | Swire | 707/204 |
| 5,644,649 A | * | 7/1997 | Schoeters et al. | 382/132 |
| 5,655,084 A | * | 8/1997 | Pinsky et al. | 705/3 |
| 5,748,173 A | * | 5/1998 | Gur | 345/629 |
| 6,044,131 A | * | 3/2000 | McEvoy et al. | 378/162 |
| 6,112,234 A | * | 8/2000 | Leiper | 709/219 |
| 6,201,249 B1 | * | 3/2001 | Yamayoshi | 250/370.11 |
| 6,324,570 B1 | * | 11/2001 | Tonchev et al. | 709/207 |
| 6,604,030 B1 | * | 8/2003 | Davis et al. | 701/9 |

FOREIGN PATENT DOCUMENTS

| | | |
|---|---|---|
| EP | 0 674 187 A1 | 9/1995 |
| EP | 0 849 933 A3 | 6/1998 |
| EP | 0 905 637 A1 | 3/1999 |
| EP | 0 919 857 A2 | 6/1999 |
| EP | 1 103 219 A2 | 5/2001 |

OTHER PUBLICATIONS

Richard W. Stevens, TCP/IP Illustrated: vol. 1, (c) 1994, Addison Wesley.*

* cited by examiner

*Primary Examiner*—Moustafa M. Meky
(74) *Attorney, Agent, or Firm*—Frishauf, Holtz, Goodman & Chick, P.C.

(57) ABSTRACT

There is described a radiographic imaging system to read radiation image stored in a radiation-image storing sheet. The radiographic imaging system includes a plurality of controllers, each of which has an image-display section; a plurality of radiation-image reading apparatus to read a radiation image stored in a radiation-image storing sheet so as to generate image data; and a network to link the plurality of controllers and the plurality of radiation-image reading apparatus; wherein the controller requests a radiation-image reading apparatus to transmit the image data, read by the radiation-image reading apparatus, to the controller. The radiation-image reading apparatus reads a sheet-discrimination information in regard to each of the radiation-image storing sheets, and transmits the sheet-discrimination information to the plurality of controllers, and one of the controllers requests the radiation-image reading apparatus to transmit the image data to the controller, based on the sheet-discrimination information sent from the radiation-image reading apparatus.

8 Claims, 12 Drawing Sheets

NETWORK SYSTEM FOR RADIOGRAPHING RADIATION-IMAGES

BACKGROUND OF THE INVENTION

The present invention mainly relates to a radiographic imaging system to read radiation image stored in a radiation-image storing sheet so as to generate image data.

Recently, there is a strong tendency to increase the efficiency and speed of the diagnosis by digitizing radiation image information of a patient generated in a hospital and by storing and electrically transmitting it. Therefore, in the field of the direct radiographing, instead of the conventional screen/film system, a radiation-image radiographing system to output the digital data utilizing the stimulable phosphor substance is frequently used.

This radiation-image radiographing system, utilizing this stimulable phosphor substance, is commonly known as "Computed Radiography (CR)". In this apparatus, a part of the radiographic energy transmitted through a subject is stored once in the stimulable phosphor substance. The energy stored in the stimulable phosphor substance can be taken out as the stimulative light by exciting it by the predetermined wavelength laser light. This stimulative light can be taken out as an electric signal by using a photoelectric conversion element such as a photo-multiplier.

The radiation-image radiographing system can be largely classified into an exclusive type radiation-image radiographing system, which cannot so simply be carried, in which the stimulable phosphor substance is housed, and a cassette type radiation-image radiographing system using a cassette in which the stimulable phosphor substance is housed, and which can be carried.

Referring to FIG. 11 showing the cassette type radiation-image radiographing system using the stimulable phosphor substance, the cassette type radiation-image radiographing system using the stimulable phosphor substance will be described below.

A cassette 6 is portable and houses a stimulable phosphor substance sheet 8 storing a portion of the radiographic energy. In a radiographing room, a subject M is positioned between a radioactive source 9 and the cassette 6, and the radioactive ray from the radioactive source 9 is irradiated toward the cassette 6. The stimulable phosphor substance sheet 8 in the cassette 6 stores a part of the irradiated radiographic energy. Then, when the cassette 6 is coupled to a radiation-image reading apparatus 1, the radiation-image reading apparatus 1 reads out the radiation image information stored in the stimulable phosphor substance sheet 8. Further, a controller 2 has a monitor to which patient information and information such as a radiographing portion relating to the image stored on the cassette 6 is inputted, and by which the image read out by the radiation-image reading apparatus 1 is confirmed.

Then, the radiation-image reading apparatus 1, in order to read-out the radiation image information stored in the stimulable phosphor substance sheet 8 in the cassette 6, irradiates excitation light onto the stimulable phosphor substance sheet and photoelectrically converts the stimulative light that is emitted from the stimulative phosphor substance sheet 8 and corresponds to the stored radiation image information. After A/D conversion, the radiation-image reading apparatus 1 outputs as the digital image data. However, high accuracy is required for these systems, and the cost is considerably high.

Further, in order to enable the radiation-image reading apparatus 1 to simultaneously hold a plurality of cassettes of sheets of film, each of which corresponds to one imaging, the radiation-image reading apparatus 1 is large. Then, in the conventional cassette type radiation-image radiographing system, the radiation-image reading apparatus 1 and its exclusive controller 2 are integrated, or separately connected in a one to one relationship. Accordingly, in many cases, one set of the radiation-image reading apparatus 1 and its exclusive controller 2 are installed per a plurality of radiographing rooms. However, the radiographing operation in the radiographing room in which this set is not installed is inconvenient, and because the time interval between the radiographing and the input of the patient information and radiographing information is long, the radiology technician (radiographic engineer) tends to make mistakes inputting information. Further, because the time until the technician goes to the radiation-image reading apparatus 1 from the radiographing room, and sets the cassette and returns to the radiographing room after the image confirmation is long, there is a problem that the instruction of the next radiographing of the patient is delayed, or the image may not be confirmed until after the photographed patient has left the radiographing room, and it is necessary to call the patient back if re-radiographing is necessary. Accordingly, although it is considered that at least one set of the radiation-image reading apparatus 1 and its exclusive controller 2 be installed in each radiographing room in the hospital, because it is installed irrespective of the frequency of the radiographing in the radiographing room, it is uneconomical, and further, the mounting space becomes large, and the cost is high.

Further, in any case, there is a problem, when any one of the radiation-image reading apparatus 1 or its controller 2 is faulty, both of them cannot be used.

Further, a system shown, in FIG. 12 is proposed as another radiographing system. In this system, when the patient information of the patient to be photographed by the cassette 6 and the information of a photographic position are inputted at the information input terminal 5, an ID number to discriminate the stimulable phosphor substance sheet 8 accommodated in the cassette 6 is simultaneously read out, and it is stored in the server 4 through the network 3 as a series of information corresponding to the patient information or radiographing position information. When the radiographing using the cassette 6 is completed, the cassette 6 is coupled to the radiation-image reading apparatus 1, and in the same manner as the radiation-image reading apparatus 1, the radiation image information stored in the stimulable phosphor substance sheet 8 in the set cassette 6 is read out. At this time, the ID number of the stimulable phosphor substance sheet 8 is also read out by the radiation-image reading apparatus 1. The radiation-image reading apparatus 1 refers to the registration information corresponding to the read out ID number in the server 4, and associates the registration information received from the server 4 with the read out radiation image information, and transfers it to an image confirmation apparatus 7. Because the registration information and the radiation image information from a plurality of radiation-image reading apparatus 1 are collected in the image confirmation apparatus 7, the final confirmation of the image is conducted therein.

In this system, a plurality of information input terminals 5 and radiation-image reading apparatus 1 are connected to the network 3. In each radiographing room of the hospital, only the information input terminal 5 is installed, and when, in a common space between the radiographing rooms, a plurality of radiation-image reading apparatus 1 are installed, the installation space can be more reduced.

However, in each radiographing room, because the image confirmation apparatus 7 is not installed, there is a problem that the radiologist who is charge of radiographing cannot confirm the image. Accordingly, a full-time person who uses the image confirmation apparatus 7 and conducts the image confirmation, is necessary, and there is a defect, which results in an increase of the human cost.

Further, when the image confirmation apparatus 7 is malfunctioned, there is a defect that the image read out by whole radiation-image reading apparatus 1 cannot be confirmed.

Accordingly, it is considered that the image confirmation apparatus 7 is installed in each radiographing room. According to this, when a nurse or an assistant goes to set the cassette 6 to the radiation-image reading apparatus 1, the radiologist can input the patient information or radiographing information or confirm the image, without going-out from the radiographing room. However, when the information input terminal 5 and the image confirmation apparatus 7 are installed in each radiographing room, there is a problem that a large installation space is necessary, and the wiring easily becomes complicated.

Further, because it is necessary that both of the information input terminal 5 and the image confirmation apparatus 7 are installed in each radiographing room, the cost is increased. Further, because it is necessary that the radiologist operates both of the controller 2 and the image confirmation apparatus 7, the operation efficiency is lowered.

Further, because the images photographed in other radiographing rooms are returned to the image confirmation apparatus 7, it takes a long period of time to find out the his own photographed image. In order to avoid this problem, in the case where the image confirmation apparatus 7 is directly connected to respective radiation-image reading apparatus 1, when either one of the radiation-image reading apparatus 1 or the image confirmation apparatus 7 is faulty, a new problem that both of them can not be used, is generated.

SUMMARY OF THE INVENTION

To overcome the abovementioned drawbacks in conventional radiographic imaging systems, it is an object of the present invention to provide a radiographic imaging system, in which a radiologist can conduct actions of inputting patient-information and radiographing-information, confirming the radiation images, changing the image-processing, etc., in regard to radiographing and reading operations at a position near to the radiographing field, and which makes it possible to provide a effective and easy working environment for users, and further, which not only makes it possible to reduce a space and a cost required for introducing apparatus concerned, but also has a high system-expandability. Further, it is another object of the present invention to provide such a reliable radiographic imaging system that, even if a certain apparatus constituting the network malfunctions, other apparatus can cope with possible troubles.

Accordingly, to overcome the cited shortcomings, the abovementioned objects of the present invention can be attained by radiographic imaging systems, described as follow.

(1) A radiographic imaging system, comprising: a plurality of controllers, each of which has an image-display section; a plurality of radiation-image reading apparatus to read a radiation image stored in a radiation-image storing sheet so as to generate image data; and a network to link the plurality of controllers and the plurality of radiation-image reading apparatus; wherein the controller requests a radiation-image reading apparatus to transmit the image data, read by the radiation-image reading apparatus, to the controller.

(2) The radiographic imaging system of item 1, wherein the radiation-image reading apparatus reads a sheet-discrimination information in regard to each of the radiation-image storing sheets, and transmits the sheet-discrimination information to the plurality of controllers, and one of the controllers requests the radiation-image reading apparatus to transmit the image data to the controller, based on the sheet-discrimination information sent from the radiation-image reading apparatus.

(3) The radiographic imaging system of item 1, wherein the controller receives an apparatus-discrimination information in regard to each of the plurality of radiation-image reading apparatus, and the controller requests the radiation-image reading apparatus to transmit the image data to the controller, based on the apparatus-discrimination information sent from the radiation-image reading apparatus.

(4) The radiographic imaging system of item 1, wherein the controller reads each of sheet-discrimination information in regard to each of the radiation-image storing sheets, and each of the radiation-image reading apparatus correlates, stores and transmits each of the image data and the sheet-discrimination information read from the radiation-image storing sheet.

(5) The radiographic imaging system of item 1, wherein the radiation-image reading apparatus correlates and stores the image data and a sheet-discrimination information read from the radiation-image storing sheet; and wherein the controller searches out a radiation-image reading apparatus, which stores the image data correlated to the sheet-discrimination information as that read by the controller, from the plurality of radiation-image reading apparatus, and then, the controller requests the radiation-image reading apparatus, searched out by the controller, to transmit the image data to the controller.

(6) The radiographic imaging system of item 1, wherein each of the plurality of radiation-image reading apparatus transmits the image data to all of the plurality of controllers.

(7) The radiographic imaging system of item 1, wherein sheet-discrimination information is given to each of the radiation-image storing sheets; and wherein the controller reads and stores the sheet-discrimination information from the radiation-image storing sheets; and wherein the radiation-image reading apparatus read the sheet-discrimination information from the radiation-image storing sheets; and wherein the radiation-image reading apparatus correlates and stores the sheet-discrimination information read and the image data generated; and wherein the radiation-image reading apparatus transmit the sheet-discrimination information and the image data to all of the plurality of controllers.

(8) The radiographic imaging system of item 1, wherein the plurality of controllers are prioritized in advance, and the radiation-image reading apparatus transmits the image data to a controller having a highest priority among receivable controllers within the plurality of controllers.

(9) The radiographic imaging system of item 1, wherein the radiation-image reading apparatus requested by the controller transmits the image data to the controller, which requested the image data to transmit.

(10) The radiographic imaging system of item 1, further comprising: a server linked to the network; wherein sheet-discrimination information is given to each of the radiation-image storing sheets; and wherein the controller reads and stores the sheet-discrimination information from the radiation-image storing sheets; and wherein the radiation-image reading apparatus read the sheet-discrimination information from the radiation-image storing sheets; and wherein the radiation-image reading apparatus correlates and stores the sheet-discrimination information read and the image data generated; and wherein the radiation-image reading apparatus transmit the sheet-discrimination information to the server; wherein apparatus-discrimination information is given to each of the radiation-image reading apparatus; and wherein the server correlates and stores the sheet-discrimination information and an apparatus-discrimination information in regard to the radiation-image reading apparatus which transmit the sheet-discrimination information; and wherein the controller selects the radiation-image reading apparatus, which stores the image data which correlated to the sheet-discrimination information that is same to the sheet-discrimination information this controller read,on the basis of the sheet-discrimination information stored in this controller and sheet-discrimination information and apparatus-discrimination information stored in the server; and wherein the controller requests the selected radiation-image reading apparatus to transmit the image data.

(11) The radiographic imaging system of item 1, wherein any of the plurality of radiation-image reading apparatus can read the radiation-image storing sheet.

(12) The radiographic imaging system of item 1, further comprising: a radiation-image reading apparatus of standing-posture or laying-posture type to includes a radiation-image storing sheet and to read radiation image stored in the radiation-image storing sheet so as to generate image data, wherein the network further link to the radiation-image reading apparatus of standing-posture or laying-posture type.

(13) A radiographic imaging system, comprising: a plurality of controllers, each of which has an image display section; a plurality of radiation-image reading apparatus to read radiation image stored in radiation-image storing sheets so as to generate image data; a server to receive the image data transmitted from the plurality of radiation-image reading apparatus and to store them; and network to link the plurality of controllers, the plurality of radiation-image reading apparatus and the server; wherein the controller requests the server to transmit an image data to the controller.

(14) The radiographic imaging system of item 13, wherein the server correlates and stores the image data and the apparatus-discrimination information in regard to each of the plurality of radiation-image reading apparatus; and wherein the controller transmits an apparatus-discrimination information to the server, and requests the server to transmit the image data correlated with the apparatus-discrimination information to the controller.

(15) The radiographic imaging system of item 13, wherein the image data and the apparatus-discrimination information are deleted after the image data is transmitted from the server to the controller.

(16) The radiographic imaging system of item 13, wherein the radiation-image reading apparatus reads sheet-discrimination information in regard to each of the radiation-image storing sheets; and wherein the radiation-image reading apparatus correlates, stores and transmits the image data and the sheet-discrimination information, to the server; and wherein the controller reads a sheet-discrimination information and transmits the sheet-discrimination information to the server; and wherein the controller requests the server to transmit the image data to the controller.

(17) The radiographic imaging system of item 13, wherein the image data and the sheet-discrimination information are deleted after the image data is transmitted from the server to the controller.

(18) A radiographic imaging system, comprising: a plurality of controllers, each of which has an image display section; a plurality of radiation-image reading apparatus to read radiation image stored in radiation-image storing sheets so as to generate image data and to read sheet-discrimination information corresponds to the radiation-image storing sheet; network to link the plurality of controllers and the plurality of radiation-image reading apparatus; wherein the radiation-image reading apparatus correlates and stores the image data and the sheet-discrimination information; and wherein the controller reads sheet-discrimination information corresponds to the radiation-image storing sheet; and wherein a controller get an image data transmitted from the network based on the sheet-discrimination information which are correlated to the image data and stored in the radiation-image reading apparatus and a sheet-discrimination information read by the controller, to the controller.

Further, to overcome the abovementioned problems, other network systems, embodied in the present invention, will be described as follow:

(1') A network system for radiographing radiation images, comprising: a plurality of controllers, each of which has an image-display section; and a plurality of radiation-image reading apparatus to read the radiation images stored in radiation-image storing sheets so as to generate image data sets each of which corresponds to each of the radiation images; wherein the plurality of controllers and the plurality of radiation-image reading apparatus are coupled each other to constitute the network system, and a controller requests a radiation-image reading apparatus, in which an image data set is currently stored, to transmit the image data set to the controller; and wherein the controller, the radiation-image reading apparatus and the image data set are one of the plurality of controllers, one of the plurality of radiation-image reading apparatus and one of the image data sets, respectively.

(2') The network system of item 1', wherein the radiation-image reading apparatus reads a sheet-discrimination information set in regard to each of the radiation-image storing sheets, to transmit the sheet-discrimination information set to the controller, and the controller requests the radiation-image reading apparatus to transmit the image data set to the controller, based on the sheet-discrimination information set sent from the radiation-image reading apparatus.

(3') The network system of item 1', wherein the controller receives an apparatus-discrimination information set in regard to each of the plurality of radiation-image reading apparatus, and the controller requests the radiation-image reading apparatus to transmit the image data set to the controller, based on the apparatus-discrimination information set sent from the radiation-image reading apparatus.

(4') The network system of item 1', wherein the controller reads each of sheet-discrimination information sets in regard to every one of the radiation-image storing sheets, and each of the radiation-image reading apparatus correlates each of the image data sets with each of the sheet-discrimination information sets to store them in it, and also transmits a sheet-discrimination information set concerned when transmitting the image data set.

(5') The network system of item 1', wherein the radiation-image reading apparatus correlates the image data set with a sheet-discrimination information set in regard to one of the radiation-image storing sheets, from which the image data set is generated, to store them in it; and wherein the controller searches out a radiation-image reading apparatus, which stores the same sheet-discrimination information set as that read by the controller, from the plurality of radiation-image reading apparatus, and then, the controller requests the radiation-image reading apparatus, searched out by the controller, to transmit the image data set to the controller.

(6') The network system of item 1', wherein each of the plurality of radiation-image reading apparatus transmits the image data sets to all of the plurality of controllers.

(7') The network system of item 6', wherein each of the plurality of controllers reads each of sheet-discrimination information sets in regard to every one of the radiation-image storing sheets, and each of the plurality of the radiation-image reading apparatus correlates each of the image data sets with each of the sheet-discrimination information sets to store them in it, and transmits the image data set and its sheet-discrimination information set to all of the plurality of controllers.

(8') The network system of item 6', wherein the plurality of controllers are prioritized in advance, and the radiation-image reading apparatus transmits the image data set to a controller having a highest priority among receivable controllers within the plurality of controllers.

(9') The network system of item 1', wherein a plurality of apparatus, including at least the plurality of controllers and the plurality of radiation-image reading apparatus, are coupled each other in the network system, and the radiation-image reading apparatus stores the image data set in it, and transmits the image data set to one of the plurality of apparatus, designated by the radiation-image reading apparatus.

(10') The network system of item 9, further comprising: a server provided for the network system; wherein the controller reads each of sheet-discrimination information sets in regard to every one of the radiation-image storing sheets, and correlates it with each of patient-information sets to transmit them to the server; and the radiation-image reading apparatus correlates each of the image data sets with each of the sheet-discrimination information sets to transmit them to the server; and the server correlates each of the image data sets with each of the patient-information sets by referring to each of the sheet-discrimination information sets to transmit the image data sets and the patient-information sets to one of the plurality of apparatus designated by the controller or the radiation-image reading apparatus.

(11') The network system of item 1', wherein the controller includes a reading device for reading data recorded in a recording medium, and each of the radiation-image reading apparatus correlates each of the image data sets with each of the sheet-discrimination information sets to store them in it and is capable of recording each of the image data sets and each of the sheet-discrimination information sets into the recording medium stored in it; and wherein the radiation-image reading apparatus records the image data set, correlated with a sheet-discrimination information set concerned, into the recording medium, and the controller is capable of reading the image data set and the sheet-discrimination information set, which are stored in the recording medium; and wherein the sheet-discrimination information set is one of the sheet-discrimination information sets.

(12') The network system of item 1', wherein the radiation-image reading apparatus includes a holding section for holding a subject in either a standing-posture or a laying-posture when radiographing the radiation images.

(13') A network system for radiographing radiation images, comprising: a plurality of controllers, each of which has an image-display section; a plurality of radiation-image reading apparatus to read the radiation images stored in radiation-image storing sheets so as to generate image data sets each of which corresponds to each of the radiation images; and a server to receive the image data sets transmitted from the plurality of radiation-image reading apparatus and to store them in it; wherein the plurality of controllers, the plurality of radiation-image reading apparatus and the server are coupled each other to constitute the network system, and a controller requests the server to transmit an image data set to the controller; and wherein the controller and the image data set are one of the plurality of controllers and one of the image data sets, respectively.

(14') The network system of item 13', wherein the radiation-image reading apparatus correlates each of the image data sets with each of apparatus-discrimination information sets in regard to every one of the plurality of radiation-image reading apparatus to transmit them to the server; and wherein the controller transmits an apparatus-discrimination information set to the server to retrieve the image data set correlated with the apparatus-discrimination information set from the image data sets stored in the server, and requests the server to transmit the image data set to the controller; and wherein the apparatus-discrimination information set is one of the apparatus-discrimination information sets.

(15') The network system of item 14', wherein the image data set and the apparatus-discrimination information set are deleted after the image data set is transmitted from the server to the controller.

(16') The network system of item 13', wherein the radiation-image reading apparatus correlates each of the image data sets with each of sheet-discrimination information sets in regard to every one of the radiation-image storing sheets to transmit them to the server; and wherein the controller reads a sheet-discrimination information set and transmits the sheet-discrimination information set to the server to retrieve the image data set correlated with the sheet-discrimination information set from the image data sets stored in the server, and requests the server to transmit the image data set to the controller; and wherein the sheet-discrimination information set is one of the sheet-discrimination information sets.

(17') The network system of item 16', wherein the image data set and the sheet-discrimination information set are deleted after the image data set is transmitted from the server to the controller.

(18') A network system for radiographing radiation images, comprising: a plurality of controllers, each of which has an image-display section; and a plurality of radiation-image reading apparatus to read the radiation images stored in radiation-image storing sheets so as to generate image data sets each of which corresponds to each of the radiation images, and to read sheet-discrimination information sets each of which corresponds to each of the radiation-image storing sheets; wherein the plurality of controllers and the plurality of radiation-image reading apparatus are coupled each other to constitute the network system, and each of the radiation-image reading apparatus correlates each of the image data sets with each of the sheet-discrimination information sets to temporarily store them in it, and the controller reads each of the sheet-discrimination information sets; and wherein a radiation-image reading apparatus transmits an image data set and a sheet-discrimination information set, which are correlated each other and temporarily stored in the radiation-image reading apparatus, to the controller, based on a sheet-discrimination information set read by the controller; and wherein the radiation-image reading apparatus, the image data set and the sheet-discrimination information set are one of the plurality of radiation-image reading apparatus, one of the image data sets and one of the sheet-discrimination information sets, respectively.

Still further, to overcome the abovementioned problems, other radiation-image radiographing systems, embodied in the present invention, will be described as follow:

(19) A radiation-image radiographing system characterized in that, in the radiation-image radiographing system, in which a controller having an image-display section and a plurality of radiation-image reading apparatus, which transmit image data obtained by reading radiation-images stored in radiation-image storing sheets, are arranged in the same network, the controller requests the radiation-image reading apparatus, which has the image data of the radiation-image read from the radiation-image storing sheet, to transmit the image data to the controller.

(20) The radiation-image radiographing system described in item 19, characterized in that, the controller requests to transmit the image data set to the controller, based on an apparatus-discrimination information of the radiation-image reading apparatus having the image data of the radiation-image read from the radiation-image storing sheet.

(21) The radiation-image radiographing system described in item 19, characterized in that, the controller reads a sheet-discrimination information of the radiation-image storing sheet, and the radiation-image reading apparatus stores the image data of the radiation-image read from the radiation-image storing sheet and the sheet-discrimination information of the radiation-image storing sheet, in it, while correlating them each other, and also transmits a sheet-discrimination information with the image data.

(22) The radiation-image radiographing system described in item 19, characterized in that, the radiation-image reading apparatus, having the image data of the radiation-image read from the radiation-image storing sheet, stores the sheet-discrimination information of the radiation-image storing sheet in it while correlating it with the image data concerned, and the controller retrieves a radiation-image reading apparatus, in which the sheet-discrimination information of the radiation-image storing sheet read by the controller are stored, from the plurality of radiation-image reading apparatus, and requests the radiation-image reading apparatus, having the image data, to transmit the image data to the controller, based on the result of retrieving.

(23) A radiation-image radiographing system characterized in that, in the radiation-image radiographing system, in which a plurality of controllers, to register a discrimination information of a radiation-image storing sheet, and a plurality of radiation-image reading apparatus, to output image data obtained by reading the radiation image stored in the radiation-image storing sheet, are arranged on the same network, the controller requests to transmit the image data to the controller concerned, even if the image data is read from a radiation-image storing sheet set in anyone of radiation-image reading apparatus designated by the controller concerned, and the radiation-image reading apparatus, which is requested to transmit the image data by the controller, transmits the image data of the radiation-image read from the radiation-image storing sheet to the controller.

According to anyone of the radiation-image radiographing systems mentioned above, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is possible to prevent a specific radiographing room from being overloaded. Still further, the control mode of both the controller side and the radiation-image reading apparatus side is advantageously simple, the development cost of the control software is low, and further, it is easily operated stably.

(24) A radiation-image radiographing system, characterized in that, in the radiation-image radiographing system, in which a controller having an image-display section and a plurality of radiation-image reading apparatus, which transmit image data obtained by reading radiation-images stored in radiation-image storing sheets, are arranged in the same network, the image data of the radiation-image read from the radiation-image storing sheet by the radiation-image reading apparatus are transmitted to all of the controllers arranged in the same network.

(25) The radiation-image radiographing system described in item 24, characterized in that, the controller reads sheet-discrimination information of the radiation-image storing sheet, and the radiation-image reading apparatus stores the image data of the radiation-image read from the radiation-image storing sheet and the sheet-discrimination information of the radiation-image storing sheet while correlating them each other and transmit the sheet-discrimination information with the image data to all of the controllers arranged in the same network.

The merit of the abovementioned radiation-image radiographing system lies in that even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is possible to prevent a specific radiographing room from being overloaded. Still further, the control mode of both of the controller side and the radiation-image reading apparatus side is simple, the development cost of the control software is low, and further, it is easily operated stably.

(26) A radiation-image radiographing system, characterized in that, in the radiation-image radiographing system, in which a controller having an image-display section, a plurality of radiation-image reading apparatus, which transmit image data obtained by reading radiation-images stored in radiation-image storing sheets, and a server, are arranged in the same network, the radiation-image reading apparatus transmits the image data of the read radiation-image to the server, and the controller requests the server to transmit the image data, which are transmitted from the radiation-image reading apparatus and stored in the server, to the controller concerned.

(27) The radiation-image radiographing system described in item 26, characterized in that, the radiation-image reading apparatus transmits the image data of the radiation-image read from the radiation-image storing sheet and apparatus-discrimination information of the radiation-image reading apparatus to the server while correlating them each other, and the controller transmits the apparatus-discrimination information to the server to retrieve the image data stored in the server, based on the apparatus-discrimination information correlated, and the controller request the server, which stores the image data as a retrieving object, to transmit the image data to the controller.

(28) The radiation-image radiographing system described in item 26, characterized in that, the radiation-image reading apparatus transmits the image data of the radiation-image read from the radiation-image storing sheet and sheet-discrimination information of the radiation-image storing sheet to the server while correlating them each other, and the controller reads sheet-discrimination information of the radiation-image storing sheet, and transmits the sheet-discrimination information of the radiation-image storing sheet to the server to retrieve the image data stored in the server, based on the sheet-discrimination information correlated, and the controller request the server, which stores the image data as a retrieving object, to transmit the image data to the controller.

(29) The radiation-image radiographing system described in item 27 or item 28, characterized in that, after the image data are transmitted from the server to the controller, the image data and the sheet-discrimination information or the apparatus-discrimination information stored in the server are deleted.

(30) A radiation-image radiographing system, characterized in that, in the radiation-image radiographing system, in which a plurality of controllers, to register a discrimination information of a radiation-image storing sheet, a plurality of radiation-image reading apparatus, to output image data obtained by reading the radiation image stored in the radiation-image storing sheet, and a server, to store discrimination information and the image data outputted by the radiation-image reading apparatus, are arranged on the same network, the radiation-image reading apparatus transmits the discrimination information and the image data of the radiation-image read from the radiation-image storing sheet, and an operator-discrimination information in respect to the radiation-image to the server on the network, and the controller, which requests the image data, transmits the operator-discrimination information in respect to the radiation-image and the controller-information as a sending end of the image data to the server, and the server retrieves the requested discrimination information and the image data by using the operator-discrimination information as a retrieving-key, and then, transmits the discrimination information and the image data to the controller serving as a sending end.

According to anyone of the radiation-image radiographing systems mentioned above, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is also possible to prevent a specific radiographing room from being overloaded.

(31) A radiation-image radiographing system characterized in that, in the radiation-image radiographing system, in which a plurality of controllers, each of which has an image-display section, and a plurality of radiation-image reading apparatus, which transmit image data obtained by reading radiation-images stored in radiation-image storing sheets, are arranged in the same network, the plurality of controllers are prioritized in advance, and the radiation-image reading apparatus transmits the image data of the radiation-image read from the radiation-image storing sheet to a controller having a highest priority among receivable controllers within the plurality of controllers.

(32) A radiation-image radiographing system, characterized in that, in the radiation-image radiographing system, in which a plurality of controllers, to register a discrimination information of a radiation-image storing sheet, and a plurality of radiation-image reading apparatus, to output image data obtained by reading the radiation image stored in the radiation-image storing sheet, are arranged on the same network, the radiation-image reading apparatus transmits the discrimination information and the image data of the radiation-image read from the radiation-image storing sheet, to the controller whose priority degree is determined in advance as a sending end.

Incidentally, it is desirable that the information of the sending end are stored in the server arranged in the same network. Further, it is also desirable that the information of the sending end are stored in each of radiation-image reading apparatus.

According to anyone of the radiation-image radiographing systems mentioned above, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is also possible to prevent a specific radiographing room from being overloaded.

(33) A radiation-image radiographing system, characterized in that, in the radiation-image radiographing system, in which a controller having an image-display section and a plurality of apparatus, including at least a plurality of radiation-image reading apparatus, which transmit image data obtained by reading radiation-images stored in radiation-image storing sheets, are arranged in the same network, the radiation-image reading apparatus stores the image data of the radiation-image, read from the radiation-image storing sheet, in it, and transmit the image data to the apparatus residing in the same network and designated by the radiation-image reading apparatus.

Incidentally, the apparatus, defined in the above, includes a viewer, a printer, a filing apparatus, etc., other than the controller and the radiation-image reading apparatus.

(34) The radiation-image radiographing system described in item 33, characterized in that, a server is further arranged on the same network, and the controller reads sheet-discrimination information of the radiation-image storing sheet, and transmits the sheet-discrimination information to the server while correlating it with patient-discrimination information, and the radiation-image reading apparatus transmits the image data of the radiation-image read from the radiation-image storing sheet and the sheet-discrimination information of the radiation-image storing sheet to the server while correlating them each other, and the server correlates the image data with the patient-information by referring to the sheet-discrimination information of the radiation-image storing sheet, and transmits the image data and the patient-information to an apparatus designated by the controller or the radiation-image reading apparatus.

(35) A radiation-image radiographing system, characterized in that, in the radiation-image radiographing system, in which a plurality of controllers, to register a discrimination information of a radiation-image storing sheet, and a plurality of radiation-image reading apparatus, to output image data obtained by reading the radiation image stored in the radiation-image storing sheet, are arranged on the same network, the radiation-image reading apparatus includes an operating means for setting a sending end, and transmits the discrimination information and the image data of the radiation-image read from the radiation-image storing sheet, to the controller, which is set as the sending end in advance by the operating means.

According to anyone of the radiation-image radiographing systems mentioned above, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is also possible to prevent a specific radiographing room from being overloaded.

(36) A radiation-image radiographing system, characterized in that, in the radiation-image radiographing system, in which a controller having a reading device for reading data recorded in a recording medium and an image-display section and a plurality of radiation-image reading apparatus, which stores the image data of the radiation-image read from the radiation-image storing sheet and sheet-discrimination information of a radiation-image storing sheet in it while correlating them each other, and which can record the stored image data and the sheet-discrimination information into the recording medium, are arranged in the same network, the radiation-image reading apparatus records the image data and the sheet-discrimination information, read from the radiation-image storing sheet and correlated each other, into the recording medium, and the controller is capable of reading the image data and the sheet-discrimination information set, which are recorded into the recording medium.

(37) The radiation-image radiographing system described in item 36, characterized in that, the controller and the radiation-image reading apparatus are arranged in the same network.

(38) A radiation-image radiographing system, characterized in that, in the radiation-image radiographing system, in which a plurality of controllers, to register a discrimination information of a radiation-image storing sheet, and a plurality of radiation-image reading apparatus, to output image data obtained by reading the radiation image stored in the radiation-image storing sheet, are arranged on the same network, the radiation-image reading apparatus includes a recording-medium handling means for recording the discrimination information and the image data into a recording medium while the controller includes a recording-medium handling means for reading the discrimination information and the image data stored in the recording medium, and the discrimination information and the image data read from the radiation-image storing sheet by the radiation-image reading apparatus are transferred to the controller through the recording medium.

According to anyone of the radiation-image radiographing systems mentioned above, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is also possible to prevent a specific radiographing room from being overloaded.

(39) The radiation-image radiographing system described in anyone of items 19–38, characterized in that, the radiation-image reading apparatus includes a holding section for holding a subject in either a standing-posture or a laying-posture when radiographing the radiation images.

(40) A radiation-image radiographing system, characterized in that, in the radiation-image radiographing system, in which a plurality of controllers, to register a discrimination information of a radiation-image storing sheet, and a plurality of radiation-image reading apparatus, to output image data obtained by reading the radiation image stored in the radiation-image storing sheet, are arranged on the same network, the radiation-image reading apparatus is capable of designating anyone of the plurality of controllers, serving as a sending end to which the image data of the radiation-image read from the radiation-image storing sheet set in it are transmitted, and transmits the image data of the radiation-image read from the radiation-image storing sheet set in it to the designated controller.

Incidentally, it is desirable that the controller designated as the sending end by the radiation-image reading apparatus is such a controller that is registered in advance by the operator.

Further, it is also desirable that the controller(s) designated as the sending end by the radiation-image reading apparatus is/are such (a) controller(s) that is/are a single or an arbitral plural number.

Still further, it is also desirable that the transmitting operation of the image data to the controller or the apparatus, designated as the sending end by the radiation-image reading apparatus, is performed at only one time, after the sending end is designated.

Still further, it is also desirable that, after the radiation-image reading apparatus designates the sending end, the image data are transmitted to the designated controller or apparatus, every time when the operation for reading the image data from the radiation-image storing sheet is completed.

The merit of the abovementioned radiation-image radiographing system lies in that, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is possible to prevent a specific radiographing room from being overloaded. Still further, the control mode of both of the controller side and the radiation-image reading apparatus side is simple, the development cost of the control software is low, and further, it is easily operated stably.

(41) A radiation-image radiographing system, characterized in that, in the radiation-image radiographing system, in which a plurality of controllers, to register a discrimination information of a radiation-image storing sheet, and a plurality of radiation-image reading apparatus, to output image data obtained by reading the radiation image stored in the radiation-image storing sheet, are arranged on the same network, the radiation-image reading apparatus is capable of designating an apparatus, serving as a sending end to which the image data of the radiation-image read from the radiation-image storing sheet set in it are transmitted, and transmits the image data of the radiation-image read from the radiation-image storing sheet set in it to the designated apparatus, which is other than the plurality of controllers.

Incidentally, it is desirable that the designated apparatus is either a host-computer or an image-outputting apparatus.

Further, it is also desirable that the transmitting operation of the image data to the controller or the apparatus, designated as the sending end by the radiation-image reading apparatus, is performed at only one time, after the sending end is designated.

Still further, it is also desirable that, after the radiation-image reading apparatus designates the sending end, the image data are transmitted to the designated controller or apparatus, every time when the operation for reading the image data from the radiation-image storing sheet is completed.

The merit of the abovementioned radiation-image radiographing system lies in that, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is also possible to prevent a specific radiographing room from being overloaded. Still further, the control mode of both of the controller side and the radiation-image reading apparatus side is simple, the development cost of the control software is low, and further, it is easily operated stably.

(42) A radiation-image radiographing system, characterized in that, in the radiation-image radiographing system, in which a plurality of controllers, to register a discrimination information of a radiation-image storing sheet, and a plurality of radiation-image reading apparatus, to output image data obtained by reading the radiation image stored in the radiation-image storing sheet, are arranged on the same network, the radiation-image reading apparatus holds the discrimination information and the image data of the radiation-image read from the radiation-image storing sheet set in it, and the controller transmits the discrimination information of a radiation-image storing sheet and controller information of a sending end, to which the image data are transmitted, in respect to a desired radiation image, and, when the radiation-image reading apparatus holds the image data corresponding to the received discrimination information, the radiation-image reading apparatus transmits the image data and the discrimination information to the controller concerned, referring to the controller information of the sending end.

According to anyone of the radiation-image radiographing systems mentioned above, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is also possible to prevent a specific radiographing room from being overloaded.

(43) A radiation-image radiographing system, characterized in that, in the radiation-image radiographing system, in which a plurality of controllers, to register a discrimination information of a radiation-image storing sheet and a plurality of radiation-image reading apparatus, to output image data obtained by reading the radiation image stored in the radiation-image storing sheet, are arranged on the same network, the radiation-image reading apparatus holds the discrimination information and the image data of the radiation-image read from the radiation-image storing sheet set in it, and the controller transmits the operator-discrimination information and controller information of a sending end, to which the image data are transmitted, in respect to a desired radiation image, and, when the radiation-image reading apparatus holds the image data corresponding to the received operator-discrimination information, the radiation-image reading apparatus transmits the image data and the discrimination information to the controller concerned, referring to the controller information of the sending end.

According to anyone of the radiation-image radiographing systems mentioned above, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is also possible to prevent a specific radiographing room from being overloaded.

(44) A radiation-image radiographing system, characterized in that, in the radiation-image radiographing system, in which a plurality of controllers, to register a discrimination information of a radiation-image storing sheet, and a plurality of radiation-image reading apparatus, to output image data obtained by reading the radiation image stored in the radiation-image storing sheet, are arranged on the same network, the radiation-image reading apparatus transmits the discrimination information and the image data of the radiation-image read from the radiation-image storing sheet set in it to the plurality of controllers on the network, and one of the plurality of controllers, which confirms that the transmitted discrimination information and image data belong to itself, transmits a confirming declaration to other controllers, and the controllers, which have received the confirming declaration, abandon the discrimination information and the image data transmitted from the radiation-image reading apparatus.

According to anyone of the radiation-image radiographing systems mentioned above, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is also possible to prevent a specific radiographing room from being overloaded.

(45) A radiation-image radiographing system, characterized in that, in the radiation-image radiographing system, in which a plurality of controllers, to register a discrimination information of a radiation-image storing sheet, a plurality of radiation-image reading apparatus, to output image data obtained by reading the radiation image stored in the radiation-image storing sheet, and a server, to store discrimination information and the image data outputted by the radiation-image reading apparatus, are arranged on the same network, the radiation-image reading apparatus transmits the discrimination information and the image data of the radiation-image read from the radiation-image storing sheet set in it and apparatus-discrimination information in respect to the radiation-image reading apparatus, by which the reading operation is performed, to the server on the network, and the controller, which requests the image data, transmits the apparatus-discrimination information of the radiation-image reading apparatus, by which the reading operation is performed, and controller information of a sending end, to which the image data are transmitted, to the server, and the server retrieves the requested discrimination information and the image data by using the apparatus-discrimination information as a retrieving-key, and then, transmits the discrimination information and the image data to the controller serving as a sending end.

According to anyone of the radiation-image radiographing systems mentioned above, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is also possible to prevent a specific radiographing room from being overloaded.

BRIEF DESCRIPTION OF THE DRAWINGS

Other objects and advantages of the present invention will become apparent upon reading the following detailed description and upon reference to the drawings in which.

DETAILED DESCRIPTION OF THE PREFERRED EMBODIMENT

Embodiments of the present invention will be described below. In this connection, the present invention is not limited to embodiments described below. Further, in the following description, although there is a description in which the meaning of the term is described, this is, to the utmost, the description of the meaning of the term in the embodiment, and the meaning of the term in the present invention is not limited to this description.

First Embodiments

Figure 1:
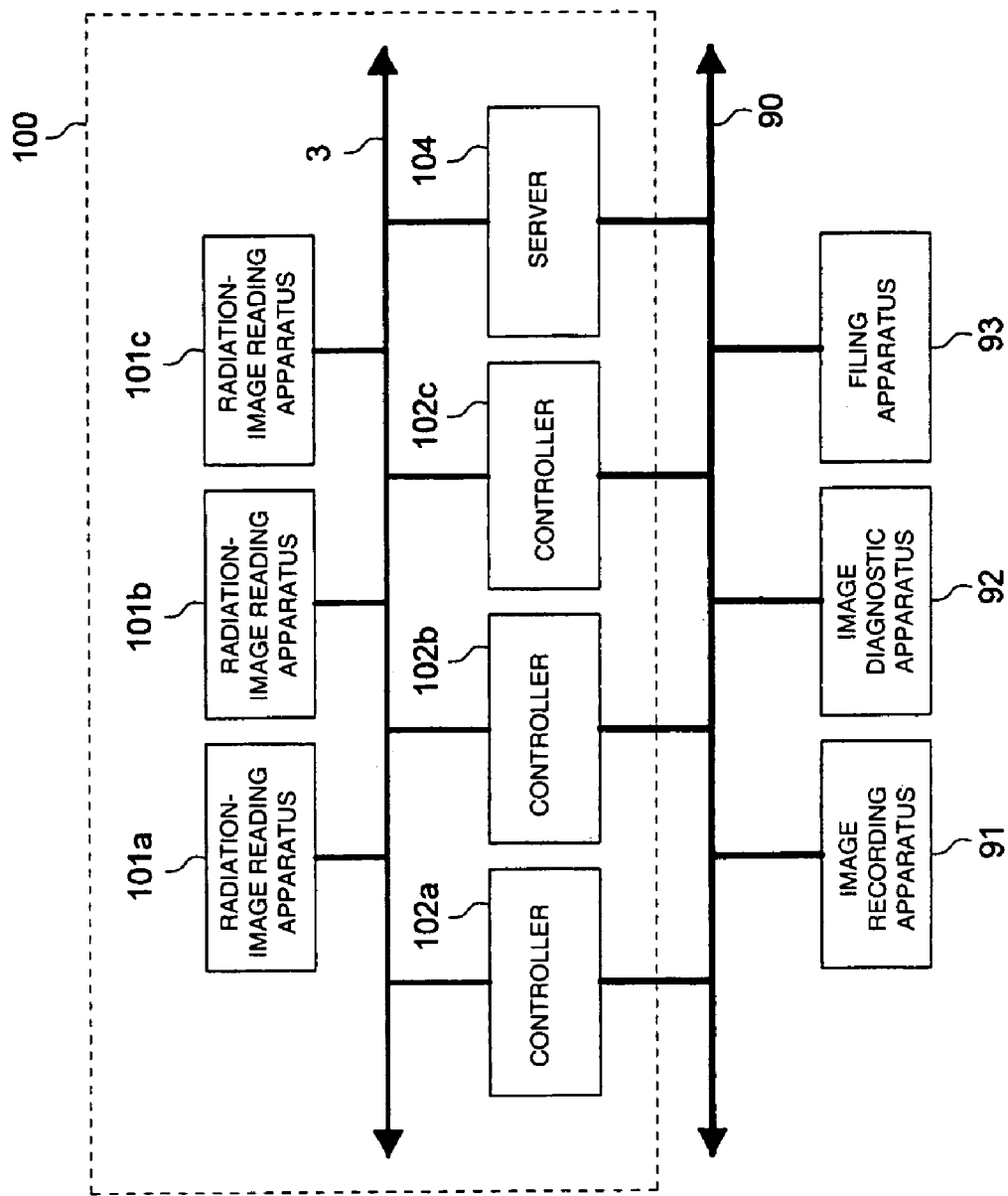
FIG. 1 shows a configuration of a radiation-image radiographing system of the first embodiment of the present invention.

In a radiation-image radiographing system 100 of the present embodiment, as shown in FIG. 1, a plurality of radiation-image reading apparatus 101a, 101b, 101c and a plurality of controllers 102a, 102b, 102c and a server 104 are connected to each other through a network 3. The plurality of controllers are connected to a DICOM network 90.

Incidentally, DICOM stands for "Digital Imaging and Communication in Medicine", which is general standards in the field.

To the DICOM network 90, an image recording apparatus 91 such as a laser imager and an image diagnostic apparatus 92 and a filing apparatus 93 and so on can be connected. The image recording apparatus 91 provides the visualized diagnostic image to the doctor, by outputting the image data, which is outputted from the controller 102, on the film, and the image diagnostic apparatus 92 provides the visualized diagnostic image to the doctor by displaying the image data outputted from the controller 102 on a monitor. The image filing apparatus 93 stores the image data outputted from the controller 102. The image data stored in the image filing apparatus 93 can be outputted at need to the image output apparatus 91 or the image diagnostic apparatus 92.

Operating Status of the First Embodiment

Initially, referring to FIG. 1 and FIG. 2, the radiation-image radiographing system 100 of the present embodiment will be described below, according to the operating statuses described in the following items (1)–(4).

Figure 2:
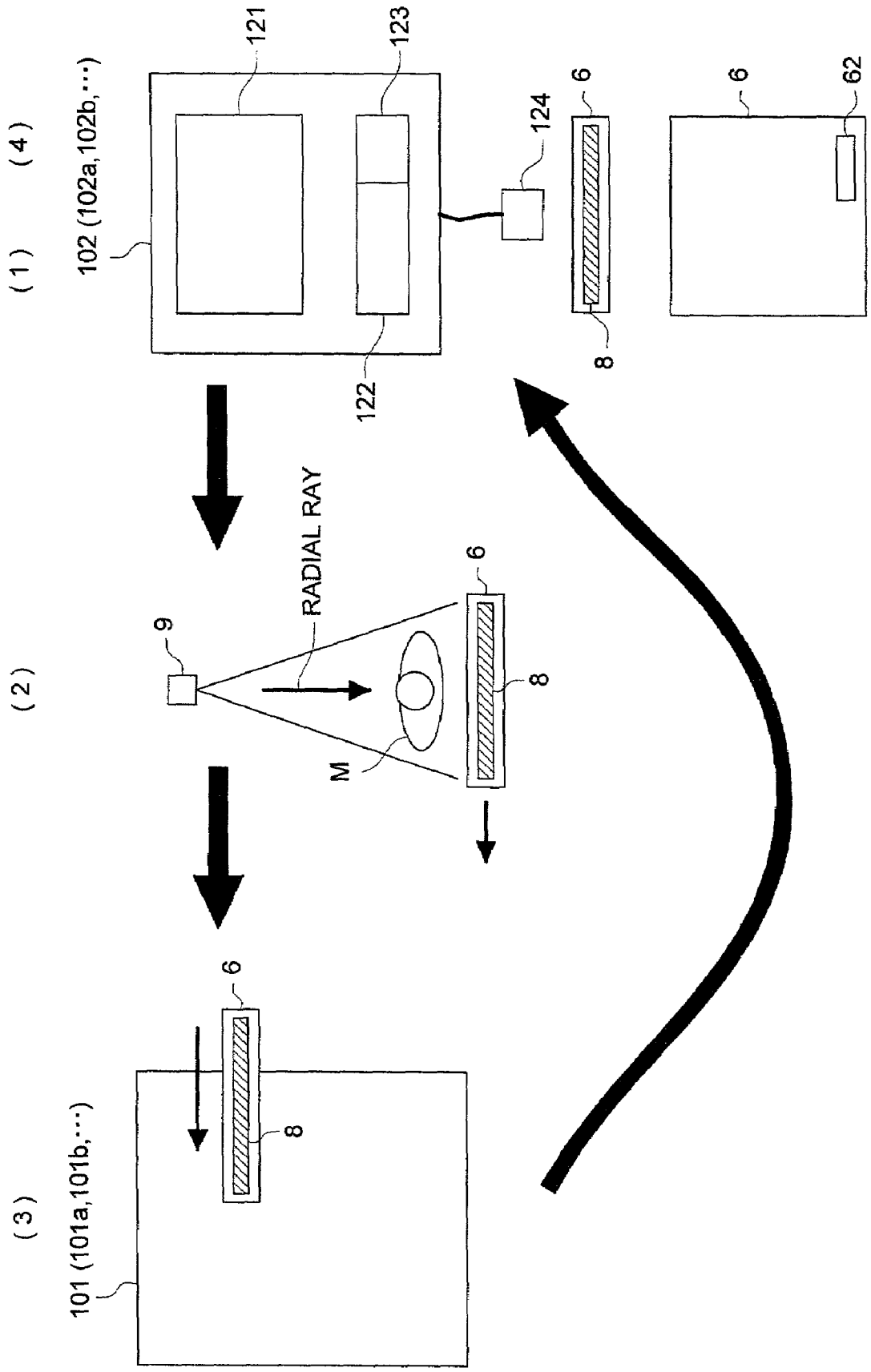
FIG. 2 shows operations of a radiation-image radiographing system of the first embodiment of the present invention.

Incidentally, although a plurality of radiation-image reading apparatus 101a, 101b, 101c are separately depicted in FIG. 1, only the radiation-image reading apparatus 101 is depicted in FIG. 2 as a representative of radiation-image reading apparatus 101a, 101b, 101c. In the same manner, although a plurality of controllers 102a, 102b, 102c are separately depicted in FIG. 1, only the controller 102 is depicted in FIG. 2 as a representative of the controllers 102a, 102b, 102c.

(1) On a casing of a cassette 6, barcode 62 corresponding to an ID number (hereinafter, the ID number is called sheet ID number) to distinguish a stimulable phosphor substance sheet 8 housed in the cassette 6 is attached. Further, in the present embodiment, although it is structured such that the sheet ID number is distinguished by the barcode 62, for example, a non-contact ID label (S label) or an element called TIRIS (Texas Instrument) in which the code which is written in the element such as a label, can be read by using the wireless engineering using the electromagnetic wave, etc., may be used instead of the barcode 62. When such the label whose code (sheet ID number) is read by using the wireless engineering is used, it is not necessary that the label is attached onto the casing of the cassette 6, and for example, the label may be attached onto the rear surface of the stimulable phosphor substance sheet 8. In this case, it would be appropriate that another label, on which the ID number for distinguishing the stimulable phosphor substance sheet 8 is written, is attached on the casing of the cassette 6.

Incidentally, it is needless to say that it is also possible to utilize a cassette ID number for distinguishing a cassette, instead of sheet ID number, as the discrimination information for distinguishing the stimulable phosphor substance sheet 8.

The radiologist brings the cassette 6 to be used for the radiographing to in front of the controller 102, and inputs the operator ID number at an operator ID input section 123 of the controller 102. As this input section, from the standpoint of accuracy of information, an optimal input device may be a finger print detector or a voiceprint detector which can distinguish the discrimination information based on the physical features, such as the finger print or voiceprint, of the operator, or an ID card reader which reads an ID card, a barcode reader which reads a barcode label, or an input device such as a portable transmission signal receiver which receives a signal from a portable transmitter. (Because the ID card, barcode label, and portable transmitter can always be carried by the operator, such devices are convenient.) Other methods, such as a key board or touch panel may also be used. Further, an input section 122 which will be described later may be structured so that it can commonly be used as the operator ID input section 123. Further, in order to neglect the troublesomeness of inputting information many times, normally, in the case where one controller is used by one person, when the input is conducted once, it is convenient that this input is set as the default. Further, the ID number of the radiologist to be used may be previously registered in the controller 102, and this may be selectable through a keyboard or touch panel.

Then, the radiologist registers the sheet ID number into the controller 102 such that the sheet ID is made to be read from the barcode 62 of the cassette 6 by using the barcode reader 124 of the controller 102, or the sheet ID is inputted from the input section 122 of the controller 102. (FIG. 2, (1))

Further, the radiologist inputs the patient information of the patient to be photographed in this cassette 6 from the input section 122, and the radiographing information when the patient is photographed. Herein, the patient information is the name of the patient, age, sex, date of birth, and patient ID to specify the patient. Further, the radiographing information is the information of the radiographing position (the information about which portion of the human body of the subject M) or radiographing method (the direction of the radiographing such as the rear front direction radiographing, front rear direction radiographing, side direction radiographing, or slanting position radiographing, or the information to specify the radiographing technique), and is not only used as the radiographing record of the patient, but also used as the image processing condition of the read-out image data, particularly the image processing parameter to determine the gradation conversion processing condition. Namely, in order to perform a good management, the image data are handled in correspondence with the patient information when sending them between sections (for instance, from the radiation-image reading apparatus to the server).

When the radiographing condition is determined, the system in which the reading condition such as the reading sensitivity or the reading resolving power (sampling pitch) of the radiation-image reading apparatus 101 is automatically selected, is provided.

In this connection, in the information, the re-usable information is stored as the default value as it is, and the input of the next time and after it may be simplified. Further, when the radiographing information or the patient information is previously registered, the structure in which the information is displayed as the list on the display section 121, and the radiologist selects the necessary information from the displayed list, may also be allowable.

The controller 102 makes the sheet ID number or operator ID number inputted from the barcode reader 124 or input section 122 correspond to a series of information such as the radiographing information or patient information, and reading condition, which are registered together with these ID numbers, (this series of information is called accompanied information), and temporarily stores them in the controller 102.

When there is an error in the sheet ID number, operator ID number, or accompanied information, displayed on the display section 121, the radiologist inputs the re-input instruction from the input section 122, and when information are correct, conducts the next input operation. Then, when these inputs are completed for all the cassettes to be photographed, the input to instruct the input completion is conducted. When the re-input instruction is inputted from the input section 122, the controller 102 clears the temporary memory such as the sheet ID number and waits the re-input.

Further, when the next sheet ID number is in putted, or the input completion is instructed, the temporarily stored sheet ID number and operator ID number and accompanied information are sent to the server 104 together with the ID number of the controller 102 (hereinafter, called controller ID number) and stored in the server 104.

When the server 104 receives these information, the server 104 registers them in the radiographing database as the record, serving as a recording file, accompanied by the photographed image proper ID number which is proper for each photographed image.

As described above, when the controller 102 registers the sheet ID number, the radiographing information corresponding to the cassette 6 is also registered together with it, and as will be described later, because the controller 102 image-processes and outputs the image data received together with the sheet ID number according to the photographic information coinciding with the sheet ID number, the registration mistake of the radiographing information due to the lapse of time as in the case where the radiographing information is registered after the image is read from the stimulable phosphor substance sheet 8 of the cassette 6, can be suppressed, and the correct image processing can be carried out.

Further, since the controller ID number is also registered together with the operator ID number and the controller ID number (utilized for distinguishing each of controllers 102*a*, 102*b*, 102*c*, - - - ) corresponding to the cassette 6 when the sheet ID number is registered by the controller 102, these information can be utilized later. In this connection, the radiation-image reading apparatus 101 also has the ID number (apparatus ID number) to distinguish each of radiation-image reading apparatus 101*a*, 101*b*, 101*c*, - - - .

(2) When a series of operations of the registration of each kind of ID numbers or the input of the accompanied information are completed, the radiologist positions the portion desired to be radioactive photographed of the subject M between the radioactive source 9 and the cassette 6 (normally, the cassette 6 is brought into contact with the subject M), and operates the radioactive ray generation control apparatus 10 of the radioactive source 9 and the radioactive ray is irradiated. Then, a part of the radioactive energy, which is irradiated from the radioactive source 9 and transmitted through the subject M, is temporarily stored in the stimulable phosphor substance sheet 8 housed in the cassette 6. (FIG. 2, (2))

(3) When the radiographing of the patient is completed, the assistant sets the cassette 6 for which the radiographing is completed, to the radiation-image reading apparatus 101. In this case, it is free to which radiation-image reading apparatus 101a, 101b, - - - the cassette 6 is set. Further, a plurality of cassettes 6 may be dispersedly set to a plurality of radiation-image reading apparatus 101a, 101b, - - - .

When the cassette 6 is set, the radiation-image reading apparatus 101 reads the sheet ID number from the barcode 62 of the cassette 6, and searches the radiographing database of the server 104 by this sheet ID number. The server 104 searches the radiographing database by the sent sheet ID number, and the newest record in the coinciding records is obtained, and returns the information of the record to the radiation-image reading apparatus 101. Then, the radiation-image reading apparatus 101 reads the radiation image information stored in the stimulable phosphor substance sheet 8 in the cassette 6 by the reading condition (reading sensitivity, or reading resolving power) described in the information of the returned record. That is, the excitation light is irradiated onto the stimulable phosphor substance sheet 8 and by the irradiated excitation light, the stimulation light emitted corresponding to the stored radiation image information is photoelectric converted, and the A/D converted digital image data (hereinafter, called image data, for simplification) is obtained. The obtained image data is transmitted to the controller 102 having the controller ID number returned from the server 104 together with the information of the record sent from the server 104.

In other words, a plurality of radiation-image reading apparatus 10i a, 101b, - - - temporarily store the image data read from the stimulable phosphor substance sheet 8 enclosed in the cassette 6 and its sheet ID number, while correlating the image data with its sheet ID number, and transmit the concerned sheet ID number to the server 104. Then, the server 104 temporarily stores the sheet ID number received from a sender apparatus, while correlating the received sheet ID number with the discrimination information of one of radiation-image reading apparatus 101a, 101b, - - - , currently serving as the sender apparatus. On the other hand, the controllers 102a, 102b, - - - retrieve the discrimination information of one of radiation-image reading apparatus 101a, 101b, - - - , based on the sheet ID number of stimulable phosphor substance sheet 8 currently read, and then, request the radiation-image reading apparatus 101 concerned to transmit the image data, based on the discrimination information of the radiation-image reading apparatus 101 retrieved. The radiation-image reading apparatus 101, which receives the request of transmission, sends the requested image data to the controller 102, which sends the request of transmission. Accordingly, since it is not necessary for the server 104 to store the image data, anyone of radiation-image reading apparatus 101a, 101b, - - - or anyone of controllers 102a, 102b, - - - can also perform that function.

When the reading of the image data is completed, the radiation-image reading apparatus 101 deletes the energy remaining on the stimulable phosphor substance sheet 8, and returns the stimulable phosphor substance sheet 8 into the cassette 6, and the cassette 6 is made in a condition that it can be taken out. The assistant returns the cassette 6 to the radiographing room, and stands by the next radiographing.

As described above, in the embodiment of the present invention, the reading condition of the stimulable phosphor substance sheet 8 is automatically determined from the registered radiographing information, and because it is structured such that the determined reading condition is stored correspondingly to the sheet ID number, the radiation-image reading apparatus 101 searches the reading condition according to the read sheet ID number, and according to the obtained reading condition, the image data can be read from the stimulable phosphor substance sheet 8 of the cassette 6. Accordingly, since the image data can be read by the appropriate reading condition, the image data with the good image quality, which is optimal to the radiographing condition, can be obtained only by registering the radiographing information by the controller 102.

(4) The radiologist conducts the confirmation operation of the received image data. Initially, while the controller 102 receives the image data from the radiation-image reading apparatus 101, the controller 102 forms the reduction image of the image data, and successively displays the reduction image on the display section 121 (FIG. 2, (4)). Further, the reduction image data is displayed together with the sheet ID number relating to the received image data or the apparatus ID number of the radiation-image reading apparatus 101 which transmits the image data, or the other accompanied information, on the display section 121. The content of these information displayed together with the image data (reduction image data) can be previously selected by the user.

When the reception of all the image data is completed, to the formed reduction image data, under the image processing condition determined by the radiographing information corresponding to the image data, the image processing such as non-linear gradation conversion processing is conducted, and displayed again on the display section 121. The radiologist confirms the image, which is displayed again, and when necessary, he can change the image processing condition, and conduct again the image processing to the reduction image data.

Further, the controller 102 notices the sheet ID number corresponding to the received image data to the server 104. The server 104 adds the information of the image transmission completion to the corresponding record in the radiographing database by this notice.

The controller 102 searches the temporarily stored information in the radiographing database in the server 104 or the controller 102 by the patient ID number, and confirms whether all the image data of the sheet ID number having the corresponding patient ID number are returned to the controller 102. When all the image data of the sheet ID number having the corresponding patient ID number are returned to the controller 102, the information that all the image data of the corresponding patient are received, is displayed on the display section 121.

It is hardly judged whether the reading of all the cassette 6 relating to one patient is completed, from the operation condition of the radiation-image reading apparatus 101, however, when all the image read from the plurality of cassettes 6 relating to the one patient are received, because the controller 102 in which the sheet ID number is registered, displays that all of them are received, the operator can step to the next operation being satisfied.

Further, in the embodiment of the present invention, the display position of the image data or the output sequence can be re-arranged in a predetermined order. These may be automatically conducted or the operator may specify it. When it is desired to be automatically conducted, the re-arranged order is previously set. For example, when it is set to be re-arranged in the registration order of the sheet ID number, even when the input order of the cassettes 6 into the radiographing apparatus 1 is random, or reception order of the image data which is received by the controller 102 is random, because the display position of the image is always determined by the registration order, there is no confusion.

Further, in the embodiment of the present invention, even when the registration of the sheet ID number of the plurality of cassettes 6 for radiographing one patient is conducted by one controller 102, and the plurality of cassettes 6 which are photographed, are dispersedly set to the plurality of radiation-image reading apparatus 101, the images read by the plurality of radiation-image reading apparatus 101 are automatically returned to the controller 102 in which the sheet ID number is registered. Therefore, even when it is the image data returned from the different radiation-image reading apparatus 101, the image data of the same patient can be collectively processed.

When the confirmation operation of the image is completed, the radiologist inputs the image determination. When the image determination is inputted, the image processing is conducted also on the image data which is not reduced, (received original image data) under the image processing condition which is finally conducted on the reduction image displayed on the display section 121, and the image processed image data is temporarily stored in the controller 102. Then, the image processed image data or the image data before the image processing, added by the image processing condition, is transmitted to the image recording apparatus 91, image diagnostic apparatus 92, or image filing apparatus 93 according to the communication protocol of the DICOM, through the DICOM network 90, together with the other accompanied information or ID information. Further, when the image determination is inputted, a code showing the processing completion is added to the record relating to the corresponding sheet ID number of the radiographing database in the server 104.

Configuration of Radiation-Image Reading Apparatus

Next, referring to FIG. 3, the internal configuration of the radiation-image reading apparatus 101 will be detailed in the following.

After the completion of the radiographing, when the cassette 6 is set to the radiation-image reading apparatus 101, the sheet ID number is read from the barcode 62 of the cassette 6 by barcode reader 150. The searching of the server 104 is conducted by the sheet ID number, and as described above, the reading condition (reading sensitivity or reading resolving power) and the controller ID number of the image data return address is obtained. According to the value of the reading sensitivity, the sensitivity of the photoelectric reading section 112 is set, and according to the value of the reading resolving power, the conveying speed of a conveying mechanism 160 or the sampling pitch of an A/D converter 113 is set.

When the cassette 6 is set to the radiation-image reading apparatus 101, the stimulable phosphor substance sheet 8 is pulled from the cassette 6, and while the stimulable phosphor substance sheet 8 is sub-scanning conveyed in the direction of X by the conveying mechanism 160, the image data stored and held in the stimulable phosphor substance sheet 8 is read out by the reading section 110.

The reading section 110 is composed of an excitation light generation section 111, photoelectric reading section 112, and A/D converter 113. While the stimulable phosphor substance sheet 8 is sub-scanning conveyed by the conveying mechanism 160, the excitation light generation section 111 irradiates the excitation light 14 for scanning in the direction perpendicular to the sub-scanning direction (main-scanning direction).

When the excitation light 14 acts upon the stimulable phosphor substance sheet 8, because the energy stored inside the fluorescent substance is generated as the stimulation light 15, the stimulation light 15 is collected, and converted into the electric signal by the photoelectric reading section 112, and the electric signal is logarithmically converted by a logarithmic converter 114 (thereby, the electric signal is converted from the electric signal which is linear to the light intensity of the stimulation light 15, into the electric signal which is logarithmically linear to the light intensity of the stimulation light 15, that is, the electric signal which is linear to the density), and further, it is digitized by the A/D converter 113.

The correction processing proper to the reading section 110 or the stimulable phosphor substance sheet 8 (the shading correction of the photoelectric reading section 112, the unevenness correction due to the excitation light generating section 111, the sensitivity unevenness correction of the stimulable phosphor substance sheet 8 and so on) is conducted on the image data outputted from the reading section 110 in the signal processing section 120, and after that, the processed data is successively, temporarily stored in the temporary storing section 130. Then, after the reading is completed, (or while the image data is read out), the communication section 140 transmits the image data to the controller 102 having the controller ID number which is returned from the server 104, through the network 3.

The image data transmitted to the controller 102 is the image data having the pixel value which is linear to the logarithm of the light intensity of the stimulation light 15, and which is improper to the diagnosis in the gradation characteristic as it is (in many cases, it can not be used for the diagnosis). In order to convert it to the image data, which can be used for the diagnosis, it is necessary that, generally, the non-linear gradation conversion processing is conducted, however, in the present embodiment, this processing is conducted in the controller 102. As described above, in the present embodiment, while the gradation characteristic, which is improper to the diagnosis, remains as it is, the image data is returned from the radiation-image reading apparatus 101 to the controller 102.

Because the processing condition of the non-linear gradation conversion processing is different depending on the radiographing position or the radiographing direction, it is necessary that the algorithm is prepared for each radiographing position or radiographing direction. Further, on the other hands, because the algorithm to automatically detect the irradiation field diaphragm of the radioactive ray at the radiographing or the subject area is necessary, the algorithm of the non-linear gradation conversion processing has generally very complicated structure.

Because the cost of the circumstances in which such complicated image processing algorithm is carried out at high speed, (called image processing circumstance), is very high, it is very uneconomical to structure the image processing circumstance on both of the radiation-image reading apparatus 101 and the controller 102. In the first embodiment, because the circumstances in which the radiologist confirms the image and then, changes the image processing condition, and under the changed image processing condition, the image processing is conducted again, is provided, the image processing circumstances are necessary on the controller 102 side. Accordingly, it is better to structure the system in such a manner that, on the radiation-image reading apparatus 101 side, the image processing is not conducted, and the image processing is conducted only on the controller 102 side. However, even when it is structured such that the image processing can be conducted on the radiation-image reading apparatus 101 side, the essence of the present invention excluding the cost is not spoiled.

Configuration of the Controller

Next, referring to FIG. 2, the controller 102 will be further detailed in the following. The controller 102 has the display section 121 to display the various information or the read images, the input section 122 for the radiologist to input the instructions, the operator ID input section 123 to input the ID of the operator such as the radiologist, and the barcode reader 124 to read the barcode 62 of the cassette 6. Further, the controller 102 is connected to the server 104 and a plurality of radiation-image reading apparatus 101 through the network 3. Further, the controller 102 can also be connected to the image recording apparatus 91, image diagnostic apparatus 92, or image filing apparatus 93 through the DICOM network 90.

As the input section 122, the key board, touch panel, or voice input apparatus can be used, but, it is not limited to them.

Further, the controller 102 or server 104 can connect to the hospital information system (HIS) or the radioactive information system (RIS). In this case, it is preferable that the patient information or the radiographing information is taken in on-line from these HIS or RIS. Further, it may be allowable that the patient is made to have a portable memory medium in which the above-described information is stored, and the memory medium reading apparatus is provided in the controller 102, and the information such as the patient information or the radiographing information is read from the potable memory medium which is brought by the patient. As such the portable memory medium and the memory medium reading apparatus, the barcode and the barcode reader, or the magnetic card and the magnetic card reader, or the IC card and the IC card reader can be listed, but, it is not limited to them.

Further, for the patient ID number, the coinciding data may be searched from the HIS, or RIS. In this case, the patient is made to have a portable memory medium in which the patient ID number is stored, and the memory medium reading apparatus is provided, and these information may be read from the portable memory medium which is brought by the patient, but, it is not limited to this, the information may be inputted from the input section 122, or the information proper to the patient such as the finger print or voice print is stored in the HIS or RIS, and the finger print detecting apparatus or voice print detecting apparatus is provided in the controller 102, thereby, by the detected finger print or voice print, the coinciding data may be searched from the HIS or RIS.

Further, as the display section 121 of the controller 102, when it is a means by which the character information or the image information can be displayed, such as the CRT display or liquid crystal display, it may be good, and as the content to be displayed, the apparatus ID number to specify the radiation-image reading apparatus 101 which obtained the image data, operator ID number, patient information, radiographing information, reading condition, radiographing condition (for example, the tube voltage of the radioactive tube, or radiation dose) obtained from the radiation generation control apparatus 10 of the radiation tube 9, information such as the number of pixels or matrix size, number of bits per 1 pixel of the image data, kind of the image processing, image processing parameter, or content of the correction processing, and the image of the photographed image data, are listed, but it is not limited to them.

Further, it may also be allowable that the radiographing position is selected by 2 steps of the rough large classification based on the main component of the human body, and further fine small classification. As an example of the large classification in this case, for example, [the head], [the chest], [the abdomen], [the upper limbs], [the lower limbs], [the backbone], [the basin]. Further, the small classification is the classification in which the position shown by the large classification is further finely classified, and for example, when the large classification is [the upper limbs], the small classification is [humeral joint], [shoulder blade], [humerus], [elbow joint], [forearm born], [hand joint], [carpus], and [finger born]. Further, the radiographing direction is generally, the radiographing direction to the human body, but, it is not limited to that. As the typical example of such the radiographing direction, [PA: Posteroanterior Projection], [AP: Anteroposterrior Projection], [LAT: lateral radiography], and [Oblique Radiography] are listed.

Further, as the kind of the image processing conducted by the controller 102, the gradation conversion processing to convert the gradation of the image data, frequency processing to convert the frequency characteristic of the image data, or dynamic range compression processing to compress the dynamic range of the image data is listed, but, it is not limited to them.

Specially, in the first embodiment, because the system is structured such that the image data having the pixel value which is linear to the logarithm of the light intensity of the stimulation light 15 is transmitted from the radiation-image reading apparatus 101 to the controller 102, it is absolutely necessary that the non-linear gradation conversion processing can be conducted by the controller 102.

Correlation Between the Radiation-Image Reading Apparatus and the Controller

As described in the above, according to the abovementioned embodiment, one of cassettes 6 can be dispersedly loaded into an arbitral one of radiation-image reading apparatus 101a - - - , irrespective of the controller 102a - - - shown in FIG. 1, which registers the sheet ID number of the cassette concerned. In addition, the image data, read by said arbitral one of radiation-image reading apparatus 101a - - - , is automatically returned to the controller 102a - - - , in which the sheet ID number of the stimulable phosphor substance sheet 8 corresponding to said image data is registered.

As described above, because the cassette whose sheet ID number is registered by one controller 102 can be set to any one of a plurality radiation-image reading apparatus 101, the low cost radiation-image reading apparatus 101 in which the number of cassettes 6 which can be set to the apparatus is small, can be used. Thereby, the installation area of the apparatus can be reduced, the introduction cost can be lowered, and the expandability can be further increased.

Further, because the cassette 6 whose sheet ID number is registered by one controller 102 can be simultaneously read out by the plurality of radiation-image reading apparatus 101, in the hospital in which many radiographing can be carried out one time for one patient, the processing ability of the radiation-image radiographing system can be increased.

Further, when "m" sets of radiation-image reading apparatus 101 in each of which "n" sheets of cassettes can be set are connected with each other, because maximum "n×m" cassettes can be continuously set, when large number of cassettes are desired to be processed once, there is no troublesomeness for the set of the cassettes, and the radiographing cycle time can be very reduced.

Further, when "m" radiation-image reading apparatus 101 are connected, because maximum "m" radiation-image reading apparatus 101 can simultaneously read the image data, as compared to the case where one radiation-image reading apparatus 101 reads the image data, the reading-out time is reduced to 1/m (the processing ability is increased to "m" times). Accordingly, also for the hospital in which many radiographing are carried out once for one patient, or the radiographing cycle is short, the ideal operation circumstance which is effective and in which there is no delay of operation, can be provided.

Further, even when a plurality of radiation-image reading apparatus 101 are used per one patient, because one controller 102 can input the patient information or accompanied information such as the radiographing condition, the input operation becomes effective.

Further, even when a plurality of radiation-image reading apparatus 101 are used per one patient, because the image data is collected in the one controller 102 in which the patient information of this patient or radiographing information is registered (that is, the sheet ID number of the stimulable phosphor substance sheet 8 used for the radiographing of this patient is registered), it is not necessary that the radiologist moves between the terminal equipment for registration of the patient information of the patient or radiographing information and the terminal equipment for the image confirmation, thereby, the operation efficiency can be increased. Further, because the registration of the patient information of the patient or radiographing information and the image confirmation can be conducted by one controller 102, the correspondence relationship between the registered information and the image data can be confirmed, thereby, the reliability of the operation can be increased.

Further, because there are a plurality of controllers 102, the controller 102 can be installed at a position near the site of the radiographing, and the radiologist can conduct the input of the patient information or radiographing information, or the confirmation of the image or selection of the image processing condition at the position near the site of the radiographing, thereby, the circumstance in which the operation efficiency is good, and the operation can be easily conducted, can be provided.

Further, even when the radiation image radiographing apparatus 1 of a portion of the plurality of radiation-image reading apparatus 101 is faulty, because the other no-faulty radiation image radiographing apparatus 1 can cope with that, the reliable system can be structured.

Further, because the server 104 collectively controls the radiographing database, its information can be referred later, and the radiographing history can be controlled without fail.

Arbitral Corresponging Operation Between
Radiation-Image Reading Apparatus and Controller
(1)

FIRST EXAMPLE OPERATION

Since the first example operation is characterized in that a plurality of radiation-image reading apparatus 101 and a plurality of controllers 102 are provided in the network system and it is possible to utilize an arbitral combination of them, it becomes possible for an arbitral controller 102 to designate an apparatus ID number of an arbitral radiation-image reading apparatus 101, and to request to send back the image data, read by the designated radiation-image reading apparatus 101, to the controller 102 concerned.

In the abovementioned first example operation, it is applicable that the controller 102 designates an apparatus ID number of an arbitral radiation-image reading apparatus 101, either before the reading operation (FIG. 2, (1)) or after the reading operation (FIG. 2, (4)).

As mentioned above, the designated radiation-image reading apparatus 101 transmits all of the stored image data or the read image data to the controller 102, which sent the requesting command.

The merit of the first example operation lies in that, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is possible to prevent a specific radiographing room from being overloaded with patients. Still further, the control mode of both of the controller 102 side and the radiation-image reading apparatus 101 side is simple, the development cost of the control software is low, and further, it is easily operated stably.

Still further, since the image data can be transmitted to a desired controller, it is possible for the operator to easily search out a desired image radiographed by him, and further, such an image confirming apparatus, etc. would not be necessary.

Still further, instead of transmitting all of the image data currently read to controllers 102a, 102b, - - - , it is also applicable that a plurality of radiation-image reading apparatus 101a, 101b, - - - , temporarily store all of the image data read and the sheet ID numbers of the stimulable phosphor substance sheets, while correlating each of the image data with its sheet ID number, and transmit all of the sheet ID numbers read from the stimulable phosphor substance sheets to all of the controllers 102a, 102b, 102c, - - - . In this case, the controllers 102a, 102b, 102c, - - - request radiation-image reading apparatus 101, serving as sender apparatus, so as to transmit the image data corresponding to the sheet ID number, which coincides with the specific sheet ID number registered in advance by the controller 102 concerned. The radiation-image reading apparatus 101, serving as sender apparatus, transmits the image data temporarily stored and correlated with the sheet ID number requested by the controller 102 concerned, to the controller 102, which has requested the transmission of the image data.

SECOND EXAMPLE OPERATION

Since the second example operation is characterized in that a plurality of radiation-image reading apparatus 101 and a plurality of controllers 102 are provided in the network system and it is possible to utilize an arbitral combination of them, it becomes possible for anyone of the radiation-image reading apparatus 101, which is currently in use of the reading operation, to designate anyone of the controllers 102 to be sent back the image data.

In the abovementioned second example operation, it is applicable that the radiation-image reading apparatus 101 can designate the controller 102 at every time of its reading operation, or the setting of the designation is effective after the designation is once set.

Further, in the abovementioned second example operation, the radiation-image reading apparatus 101 can designate either anyone of the controllers 102, arbitral number of the controllers 102 or all of the controllers 102 coupled in the network, as the controller(s) to be sent back the image data Still further, in the abovementioned second example operation, the radiation-image reading apparatus 101 can designate either a host-computer (not shown in the drawings) or the image output apparatus 91 other than the controllers 102, as another destination to be sent back the image data.

The radiation-image reading apparatus 101, in which the destination of the image data is designated in advance in the abovementioned manner, transmits all of the image data stored in it and the image data currently read to the controller(s) 102 designated.

The merit of the second example operation lies in that, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is possible to prevent a specific radiographing room from being overloaded. Still further, the control mode of both of the controller 102 side and the radiation-image reading apparatus 101 side is simple, the development cost of the control software is low, and further, it is easily operated stably.

Still further, since the image data can be transmitted to a desired controller, it is possible for the radiographic engineer to easily search out a desired image radiographed by himself, and further, such an image confirming apparatus, etc. would not be necessary.

Arbitral Corresponding Operation Between Radiation-Image Reading Apparatus and Controller (2)

With respect to the second example of the arbitral corresponding operation between the radiation-image reading apparatus and the controller, the operations employing the first–sixth solutions will be detailed in the following. Although, referring to concrete examples, a case when the transmission from the radiation-image reading apparatus to the controller is impossible and an emergency case will be detailed in the following, it is also possible to obtain good results in respect to the arbitral corresponding operation by employing the first-sixth solutions even when the operation is in a normal condition, without limiting to the above cases.

Arbital Corresponding Operation: When Transmission From Radiation-Image Reading Apparatus to Controller is Impossible Next, in the first embodiment, when the radiation image read from the stimulable phosphor substance sheet 8 of the cassette 6 by the radiation-image reading apparatus 101, is tried to be transmitted to the specified controller 102, the case where it can not be transmitted to the controller 102, will be described.

Such the case occurs due to, for example, the connection failure of the terminal of the network, runaway of the CPU due to the bug in the program or the heat generation, or malfunction or failure of the component such as the hard disk drive. Further, when it is tried to be transmitted to the specified controller 102, whether it cannot be transmitted to the controller 102, can be detected by detecting that communications cannot be established. Further, when an alarm device which emits alarm by the control from the radiation-image reading apparatus 101 or server 104, or displays the alarm is provided, or when a means for detecting the communication fault is provided in the controller 102 and the communication fault is displayed, it is noticed to the radiologist that the using controller 102 has the communication fault.

As the resolving means when the communication fault is detected, the 6 solutions, described in the following items 1)–6), are considered. These may be appropriately selected according to the convenience of the hospital side.

1) First Solution:

The first solution is to specify the controller 102 of the transmission destination of the image data from the other controller 102. This method includes further 3 solutions described in the following items 1-a)–1-c).

1-a) This solution is a method in which the user selects the other controller 102, and directly sends the controller ID number of the return address to the radiation-image reading apparatus 101 holding the image data desired to receive, and requires the return of the image data.

The radiation-image reading apparatus 101, which receives the request, transmits all of the image data stored in the radiation-image reading apparatus 101 to the controller 102 having the specified controller ID number.

The merit of this solution is that the control mode of both of the controller 102 side and the radiation-image reading apparatus 101 side is simplest, and the development cost of the control software is low, and the system can be easily operated stably.

1-b) This solution is the method in which the user selects the other controller 102, and registers the operator ID number by the selected controller 102, and sends the operator ID number and the controller ID number of the return address to all of the radiation-image reading apparatus 101, and requires the return of the image data having the transmitted operator ID number.

When the radiation-image reading apparatus 101, which receives this request, holds the image data having the required operator ID number, the image data having the required operator ID number is transmitted to the controller 102 having the specified controller ID number.

1-c) This solution is the method in which the user selects the other controller 102, and registers the operator ID number by this selected controller 102, sends the operator ID number and the controller ID number of the return address to the server 104, and requires the return of the image data having the transmitted operator ID number.

When the system is set in such a manner that the radiation-image reading apparatus 101 whose communication is not established, always searches the server 104, at the time point when the server 104 receives the request, the radiation-image reading apparatus 101 can take in this request. The radiation-image reading apparatus 101 which takes in this request transmits the image data having the required operator ID number to the controller 102 having the specified controller ID number.

The merit of the solutions described in item 1-a) and item 1-b) is: by using the operator ID number, the other controller 102 can receive the image data which is desired to be received by the user, selectively and simply. Because the image data is received by using the operator ID number as a key word, the possibility that the image data to be received by the other controller, is received by mistake, can be avoided.

2) Second Solution:

The second solution is the method in which the radiation-image reading apparatus 101 compulsively transmits the image data together with the additional information showing the secondary distribution data to all the other controllers 102, which are not faulty.

The controller 102 which received the image data and additional information temporarily saves the received image data and additional information, and when they become unnecessary, the controller 102 deletes them. For example, when the user selects the other controller 102, the determination declaration that the temporarily saved image data and the additional information are its own data and information, is conducted. When this determination declaration is transmitted to the other controllers 102, the other controllers 102 can delete the temporarily saved image data and additional information.

For example, the operator ID number may also be used for the declaration method of this determination declaration. In this case, the operator ID number in which the sheet ID number is registered is included in the additional information sent by the radiation-image reading apparatus 101. Then, when the user selects the other controller 102, the operator ID number is registered by the selected controller 102. The controller 102 compares the newly registered operator ID number with the operator ID number in the temporarily saved additional information, and when these coincide with each other, the controller 102 considers that the determination declaration is conducted.

The merit of this solution is that, when the user selects the other controller 102, because the image data is already received, (because the provability that the image data is received, is high), the image confirmation can be instantaneously conducted by using the arbitrary controller 102.

3) Third Solution:

The third solution is that the image save function is provided in the server 104, and the radiation-image reading apparatus 101 transmits the image data to the server 104 as a substitute of the transmission of the image data to the specified controller 102, and the server 104 temporarily saves the transmitted image data.

When the user selects the other controller 102 and the transmission of the temporarily saved image data is required from the selected controller 102 to the server 104, the temporarily saved image data is transmitted from the server 104 to the controller 102, which has required.

For example, in the case where the transmission of the temporarily saved image data is required from the controller 102 to the server 104, when the operator ID number is used, it is convenient. That is, when the user selects the other controller 102, the operator ID number is registered by the selected controller 102. Then, when the transmission of the temporarily saved image data is required to the server 104, the operator ID number is also sent to the server 104. The server 104 finds out the image data having the same ID number as the sent operator ID number from the temporarily saved image data, and returns it to the controller 102.

The merit of this solution is that, because the transmission destination of the image data from the radiation-image reading apparatus 101 is always fixed to the server, the development of the control software on the radiation-image reading apparatus 101 side is simple, and the development cost is low, and by simple control, the system is stably moved. Further, because the image data is searched by making the operator ID number the key word, the possibility that the image data which is tried to be received by the other controller is received by mistake, can be avoided.

4) Fourth Solution:

The fourth solution is the method in which, when the transmission to the controller 102 to which the image data is to be originally transmitted, can not be conducted, the order of the controller 102 to be transmitted is previously determined, and according to the order, the transmission of the image data is conducted to the next ordered controller 102. In this case, when the controller 102 has the communication fault, it is preferable that the user previously knows the controller 102 to be transmitted.

The merit of this solution is that, even when the user conducts nothing, the image data is automatically transmitted to the predetermined another controller 102.

5) Fifth Solution

The fifth solution is the method in which a function for specifying the controller 102 to transmit the image data is provided in the radiation-image reading apparatus 101, and the user uses this function and specifies the controller 102 to return the image data. When the user specifies the controller 102 which can be communicated, the image data is transmitted to the controller 102. Further, when the system is structured in such a manner that a plurality of controllers 102 or servers 104 can be simultaneously specified, it is further convenient.

The merit of this solution is that the control mode of both of the controller 102 side and the radiation-image reading apparatus 101 side is simple, and the development cost of the control software is low, and further, it is easily moved stably. Further, because the plurality of controllers 102 and servers 104 can be specified as the transmission destination, the system with the high safety can be structured.

6) Sixth Solution

The sixth solution is the method in which the writing apparatus of the portable memory medium is also provided in all of radiation-image reading apparatus 101, and further, in all of controllers 102, the reading apparatus of this portable memory medium is provided, and the image data which can not be returned is stored in the portable memory medium, and the portable memory medium is set in the other controller 102 and the image data is transferred into the controller 102.

As such the portable memory means, photo-magnetic disk, magnetic disk, optical disk, memory card, and portable hard disk drive are listed, but, it is not limited to them.

The merit of this solution is that, even when whole of the network 3 has the communication fault, the system can cope with it.

As described in the above items 1)–6), in the present embodiment, even when the image data read out by the radiation-image reading apparatus 101 can not be transmitted to the specified controller 102, because the image data can be transmitted to another controller 102, even when the controller of a portion in a plurality of controllers 102 has the fault during its use, another controller 102 can cope with it, and the system which is easily used and reliable can be provided.

As mentioned above, it is possible to constitute the network so that the priority order or the degree of priority, for transmitting the image data from a specific radiation-image reading apparatus 101 to a plurality of controllers 102, is determined and attached to each of the controllers 102 in advance, and, when transmitting the image data, the specific radiation-image reading apparatus 101 tries to transmit the image data to one of the controllers 101 having the high priority order or the high degree of priority at first, and, if the transmission of the image data is failed, the specific radiation-image reading apparatus 101 tries to transmit the image data to the next one of controllers 101 in order of high to low priorities. Accordingly, in the abovementioned network, even if a part of the plurality of controllers 102 eventually malfunctions in the mid-course of the network operation, other controllers 102 can cope with the trouble. Thus, it becomes possible to provide an easy-operational and reliable network system.

Further, except for the fourth solution, there is a merit that the radiologist can select the controller 102 corresponding to the using condition of a plurality of controllers 102 when the communication fault is generated.

Further, when the specified controller 102 commonly has the function of the server 104, even when the server 104 is faulty, because all the record of the radiographing database is saved in the controller 102, there is no trouble for the radiographing operation. It is further preferable when all of the controller 102 commonly have the function of the server 104.

Operation for an Arbital Correspondence: Reading Operation in Case of Emergency Next, in the case of emergency, the case in which, leaving the registration relating to the patient or radiographing till later on, it is desired that the reading out of the radiation image is conducted first, will be described, referring to the abovementioned solution described in items 1)–6), according to the procedures of items (1)–(3) described in the following.

(1) The radiologist positions a portion which is desired to be radioactive photographed, of the subject M between the radioactive source 9 and the cassette 6, and operates the radiation generation control apparatus 10 of the radioactive source 9 and irradiates the radiation. Then, a portion of the radiation energy which is irradiated from the radioactive source 9 and penetrated the subject M is stored once in the stimulable phosphor substance sheet 8 housed in the cassette 6.

(2) When the radiographing of the patient is completed, the assistant sets the cassette 6 to which the radiographing is completed, in the radiation-image reading apparatus 101. When the cassette 6 is set to the radiation-image reading apparatus 101, the apparatus 1 reads the sheet ID number from the barcode 62 of the cassette 6, and the radiographing database of the server 104 is searched by this sheet ID number. The server 104 searches the radiographing database by the sent sheet ID number, but the newest record can not be obtained in the coincided records. Accordingly, it returns the answer that there is no coincided record, to the radiation-image reading apparatus 101. The radiation-image reading apparatus 101 reads out the image data under the default reading condition, and the read out image data is temporarily stored in the radiation-image reading apparatus 101. Next, it is desired that the controller 102 to transmit the image is specified, but it is unknown to which controller 102 the image may be transmitted. In this case, it can be solved by the similar solutions as the case of the above-described communication fault. These solutions may be appropriately selected corresponding to the convenience of the hospital.

1) First Solution:

The first solution is the method in which the controller 102 of the transmission destination is specified from the controller 102 side. That is, from the controller 102, the controller ID number of the return address is directly sent to the radiation-image reading apparatus 101 holding the image data, which is desired to be received, and the return of the image data is required.

The radiation-image reading apparatus 101 received this request transmits all the holding image data together with the additional information such as the read sheet ID number, and reading condition, to the controller 102 having the specified controller ID number.

The merit of this solution is that the control mode of both of the controller 102 side and the radiation-image reading apparatus 101 side is simplest, and the development cost of the control software is low, and further, the system can be easily moved stably.

2) Second Solution:

The second solution is the method in which the radiation-image reading apparatus 101 compulsively transmits the image data together with the additional information such as the information showing the after registration data, or the read out sheet ID number, and read out condition, to all the controller 102. The controller 102 which receives the image data and the additional information temporarily saves the received image data and the additional information, and when they become unnecessary, they are deleted. For example, when the user selects another controller 102, the determination declaration to determine that the temporarily saved image data and the additional information are its own data and information, is conducted. When this determination declaration is transmitted to the other controllers 102, the other controllers 102 can delete the temporarily saved image data and the additional information.

The merit of this solution is that, when the use r selects the other controller 102, because the image data is already received (because the provability that it is received is high), the image confirmation can be immediately made by the arbitrary controller 102.

3) Third Solution:

The third solution is the method in which the image save function is provided to the server 104, and the radiation-image reading apparatus 101 transmits the image data together with the additional information such as the information showing the after registration data, read out sheet ID number, and reading out condition, and the server 104 temporarily saves the transmitted image data and the additional information.

When the user requires the transmission of the temporarily saved after registration image data from the controller 102 to the server 104, the temporarily saved image data and its additional information is transmitted from the server 104 to the controller 102.

The merit of this solution is that, because the transmission destination of the image data from the radiation-image reading apparatus 101 is always fixed to the server, the development of the control software on the radiation-image reading apparatus 101 side is simple, the development cost is low, and the system can be stably moved by the simple control.

4) Fourth Solution:

The fourth solution is the method in which the order of the controller 102 which transmits in the case of the after registration data is previously determined, and according to the order, the image data is transmitted to the controller 102 together with the additional information such as the information showing the after registration data, read out sheet ID number, and read out condition. In this case, it is preferable that the user previously knows the controller 102 to be transmitted in the case of the after registration data.

The merit of this solution is that, the image data is automatically transmitted to the predetermined another controller 102 without the user operating anything.

5) Fifth Solution:

The fifth solution is the method in which a function for specifying the controller 102 to return the image data is provided in the radiation-image reading apparatus 101, and the user uses the function and specifies the controller 102 to which the image data is returned. When the user specifies the controller 102, the image data is transmitted to the controller 102 together with the additional information such as the information showing the after registration data, read out sheet ID number, and read out condition. Further, it is further convenient when the system is structured such that a plurality of controllers 102 or servers 104 can be simultaneously specified.

The merit of this solution is that the control mode of both of the controller side and the radiation-image reading apparatus 101 side is simple, and the development cost of the control software is low, and further, the system can be easily moved stably. Further, because the a plurality of controllers 102 and servers 3 can be specified as the transmission destination, the system with the high safety can be structured.

6) Sixth Solution:

The sixth solution is the method in which the writing apparatus of the portable memory medium is provided in any radiation-image reading apparatus 101, and further, the reading apparatus of this portable memory medium is provided in any controller 102, and the image data is stored in the potable memory medium together with the additional information such as the sheet ID number which is read out the image data, and the reading condition, and the potable memory medium is set to the desired controller 102, and the image data and the additional information are transferred to the controller 102.

The merit of this solution is that, even when the whole the network 3 has the communication fault, the system can cope with it. As described above, in the case of emergency, even when, leaving the registration relating to the patient and the radiographing till later on, the reading out is conducted first, the transmission of the read out image data can be conducted to the controller 102.

(3) The radiologist inputs the patient information when the radiographing is conducted by the cassette 6, and additional information such as the radiographing information from the input section 122 of the controller 102. When the patient information or the radiographing information is determined, the controller 102 conducts the image processing under the image processing condition determined according to the radiographing information on the received image data, and displays the image processed image data on the display section 121. After that, the radiologist can change the image processing condition at need. When the change of the image processing condition is inputted, the controller 102 image processes the image data under the changed image processing condition, and displays on the display section 121 again. The controller 102 temporarily stores the inputted patient information or accompanied information such as the radiographing information, or operator ID number together with the reading condition.

When there is an error in the information displayed on the image display section 121, the radiologist can correct it by inputting the re-input instruction from the input section 122. Then, when these inputs relating to all the received image data are completed, the input instructing the input completion is conducted.

When a series of processing or input operation is completed and the image data or accompanied information is determined, the temporarily stored sheet ID number, operator ID number, reading condition, or accompanied information is transmitted together with the ID number of the controller 102 (hereinafter, called controller ID number) to the server 104.

The server 104 adds the radiographing image proper ID number for each radiographing image to the received sheet ID number, operator ID number, reading condition, or accompanied information, and registers this record in its radiographing database.

Second Embodiment

The second embodiment is a modified embodiment of the first embodiment, and is an embodiment in which the function of the server 104 of the first embodiment is not used (even when there is no server, the system can be operated). The points at which the second embodiment is different from the first embodiment will be detailed in the following. In addition, the same descriptions as those for the first embodiment will be omitted in the following.

According to the second embodiment, the sheet ID number or reading condition (reading sensitivity or reading resolving power) is registered by the controller 102, and these are determined, then, these information including at least sheet ID number are transmitted together with the controller ID number (normally, controller ID number of the controller 102 in which the sheet ID number or reading condition is registered) of the controller 102 of the return address, to all or predetermined specified radiation-image reading apparatus 101. In other words, before the cassette 6 in which the sheet ID number is registered is set to any of the radiation-image reading apparatus 101, the transmission of the image data is previously required to a plurality of radiation-image reading apparatus 101.

In the present embodiment, the image data transmission request notice in which the information such as the sheet ID number, reading condition, and controller ID number of the return address is written is formed, and this image data transmission request notice is transmitted to all of the radiation-image reading apparatus 101.

The radiation-image reading apparatus 101 received the image data transmission request notice temporarily stores the received image data transmission request notice. At an arbitrary timing, the cassette 6 is set to the radiation-image reading apparatus 101, and when the sheet ID number is read from the barcode 62 of the cassette 6, the apparatus 1 searches whether the same sheet ID number as the sheet ID number read from the barcode 62 by the radiation-image reading apparatus 101 exists in all of the image data transmission request notice temporarily stored in the radiation-image reading apparatus 101. When the coincided sheet ID number is detected, the controller ID number of the return address is obtained from the image data transmission request notice, and it is noticed to the controller 102 having this controller ID number that the cassette 6 having the desired sheet ID number is detected.

In the present embodiment, the ID detection notice in which the detected sheet ID number and its own apparatus ID number are written is formed, and this ID detection notice is transmitted to the controller 102 of the return address.

Further, the radiation-image reading apparatus 101 reads the image data from the stimulaitve fluorescent substance sheet 8 included in the cassette, according to the reading condition specified in the corresponding image data transmission request notice, and transmits the read out image data to the controller 102 of the return address.

When the coincided sheet ID number cannot be discovered, the same countermeasure as in the above described [in the case of the emergency, the case where, leaving the registration relating to the patient or radiographing till later on, the reading is conducted first] may be taken.

When the controller 102 receives the ID detection notice, it is temporarily stored in the controller 102, and checks the sheet ID number written in the received ID detection notice, and confirms that, to which image data transmission request notice, the corresponding sheet ID number is detected.

Next, the request to cancel the image data transmission request notice corresponding to the detected sheet ID number is transmitted to the radiation-image reading apparatus 101 from which at least the ID detection notice is transmitted. In the present embodiment, the cancellation request notice in which the detected sheet ID number is written, is transmitted to all of the radiation-image reading apparatus 101 from which the ID detection notice is not transmitted.

The radiation-image reading apparatus 101 received the cancellation request notice searches the image data transmission request notice having the same sheet ID number as the sheet ID number described in the cancellation request notice in all of temporarily stored image data transmission request notice, and cancels (erase) this.

The timing at which the controller 102 transmits the cancellation request notice to the radiation-image reading apparatus 101, may be before the image data is received, or after it. In this connection, the system is structured in such a manner that, when the sheet ID number corresponding to the image data transmission request notice is detected in the radiation-image reading apparatus 101, the ID detection notice is transmitted from the radiation-image reading apparatus 101 to the controller 102, and when the controller 102 receives this, and transmits the cancellation request notice to the radiation-image reading apparatus 101 from which at least the ID detection notice is not transmitted, the image data transmission request notice which becomes unnecessary, is cancelled, but, by using the other means, the image data transmission request notice which becomes unnecessary, may be cancelled. For example, the request to cancel the image data transmission request notice having the detected sheet ID number may be noticed from the radiation-image reading apparatus 101 which detected the sheet ID number to the other radiation-image reading apparatus 101.

Third Embodiment

Figure 4:
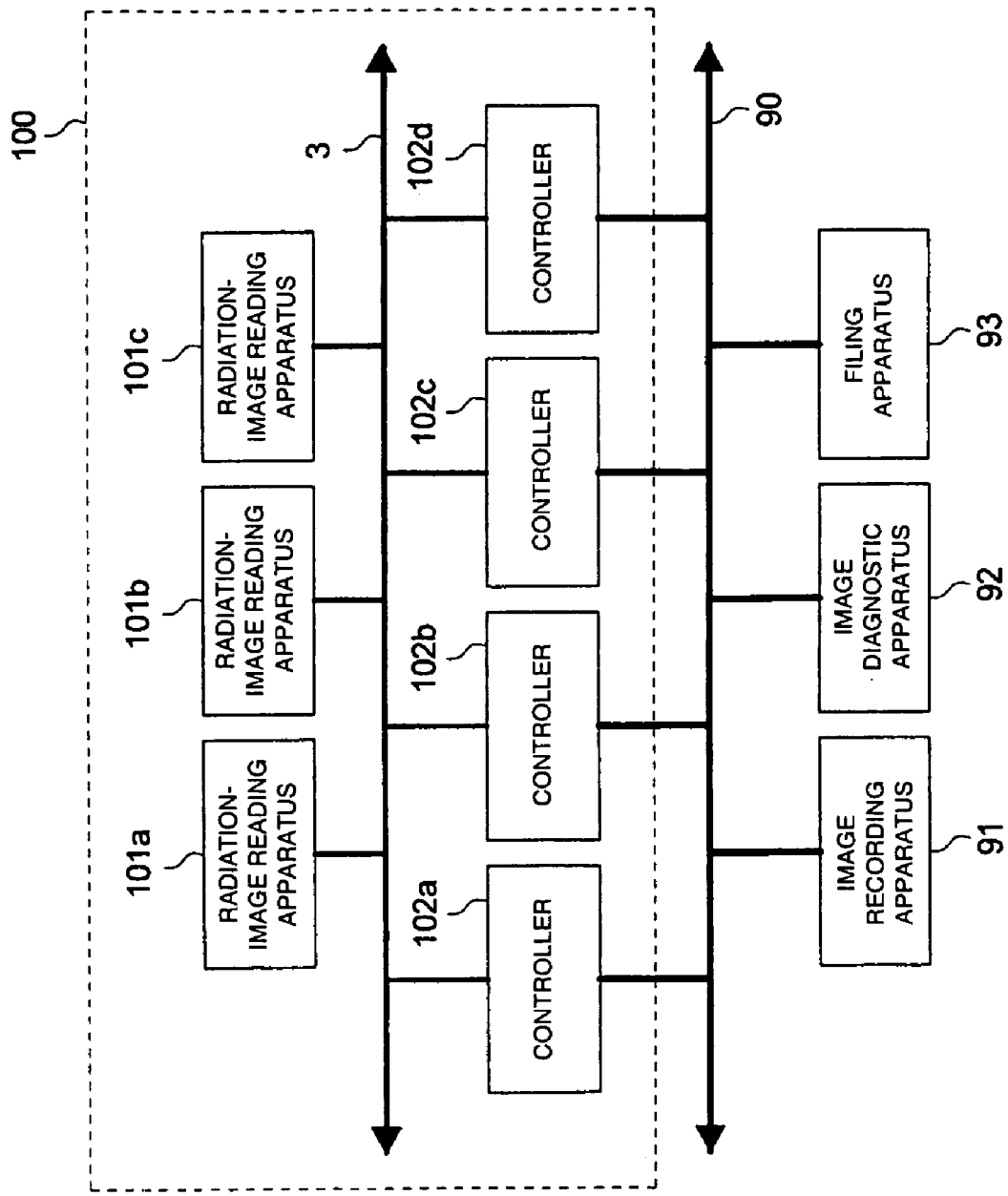
FIG. 4 shows a configuration of a radiation-image radiographing system of the second and third embodiments of the present invention.

As shown in FIG. 4, the third embodiment is a modified embodiment of the second embodiment. The points at which the third embodiment is different from the second embodiment will be detailed in the following. In addition, the same descriptions as those for the second embodiment will be omitted in the following.

According to the third embodiment, when the sheet ID number or reading condition (reading sensitivity, or reading resolving power) is registered by the controller 102, these information are temporarily stored in the controller 102. However, different from the second embodiment, the controller 102 does not transmit the image data transmission request notice in which the information such as sheet ID number, reading condition, and controller ID of the return address, is written, to the radiation-image reading apparatus 101 at this point.

When the cassette 6 is set to the radiation-image reading apparatus 101 and the sheet ID number is read from the barcode 62 of the cassette 6, at least read sheet ID number and its own apparatus ID are noticed to all of the controllers 102. In the present embodiment, the ID detection notice in which the read sheet ID and its own apparatus ID number are written is formed, and this ID detection notice is transmitted to all of the controllers 102.

Further, when the controller 102 receives the ID detection notice, this is temporarily stored in the controller 102, and the controller 102 searches whether the same sheet ID number as the sheet ID number written in the ID detection notice exists in the information temporarily stored in the controller 102. When the corresponding sheet ID number is detected, the transmission of the image data is required to the radiation-image reading apparatus 101 from which the ID detection notice is transmitted.

In the present embodiment, the controller 102 forms the image data transmission request notice in which the information such as the sheet ID number, reading condition, and controller ID of the return address is written, and transmits it to the radiation-image reading apparatus 101 from which the ID detection notice is transmitted.

When the corresponding sheet ID number can not be discovered in the information temporarily stored in the controller 102, the same countermeasure as in the above described [in the case of the emergency, the case where, leaving the registration relating to the patient or radiographing till later on, the reading is conducted first] may be taken.

Next, the request to cancel the image data transmission request notice corresponding to the detected sheet ID number is transmitted to the radiation-image reading apparatus 101 from which at least the ID detection notice is transmitted. In the present embodiment, the cancellation request notice in which the detected sheet ID number is written, is transmitted to all of the radiation-image reading apparatus 101 from which the ID detection notice is not transmitted.

The radiation-image reading apparatus 101 received the cancellation request notice searches the image data transmission request notice having the same sheet ID number as the sheet ID number described in the cancellation request notice in all of temporarily stored image data transmission request notice, and cancels (erase) this.

When the radiation-image reading apparatus 101 receives the image data transmission request notice, the image data is read from the stimulable phosphor substance sheet 8 included in the cassette 6 according to the reading condition specified in this packet, and the read out image data is transmitted to the controller 102 specified by the controller ID number of the return address in the image data transmission request notice.

The timing at which the controller 102 transmits the cancellation request notice to the radiation-image reading apparatus 101, may be before the image data is received or after it.

As described above in the second embodiments and the third embodiment, in the mode in which the function of the server 104 is not used, the radiation-image radiographing system by which the same effect as in the first embodiment can be obtained, can be structured.

Further, also in the second embodiments and the third embodiment, when the radiation image which is read from the stimulable phosphor substance sheet 8 of the cassette 6 by the radiation-image reading apparatus 101 is tried to be transmitted to the specified controller 102, there is a case where the transmission to the controller 102 can not be conducted. In this case, in the solutions as described in the first embodiment, by the solution in which the server 104 is not used, this problem can be avoided.

Further, also in the second embodiments and the third embodiment, there is a case where, in the case of emergency, leaving the registration relating to the patient or radiographing till later on, it is desired that the reading of the radiation image is conducted first. In this case also, in the solutions as described in the items 1)–6) of the first embodiment, by the solution in which the server 104 or the operator ID number is not used, this problem can be avoided.

Further, in the third embodiment, even a cassette 6 whose sheet ID number is registered by any controller 102, because it can be dispersedly set to arbitrary radiation-image reading apparatus 101, and the function to realize that the image data read out by the arbitrary radiation-image reading apparatus 101 is automatically returned to the controller 102 in which the sheet ID number of the stimulable phosphor substance sheet 8 corresponding to the image data is registered, is provided in respective controller 102 and the radiation-image reading apparatus 101, thereby, this function can be realized not though the specified server 104, accordingly, when the function of the server 104 is broken down, there is no possibility that the whole system does not function. Further, even when any controller 102 or radiation-image reading apparatus 101 has the fault, the automatic return function of the image data is not lost.

Fourth Embodiment

The fourth embodiment, which is the further modified embodiment with respect to the first, second and third embodiments mentioned above, will be detailed in the following.

Figure 3:
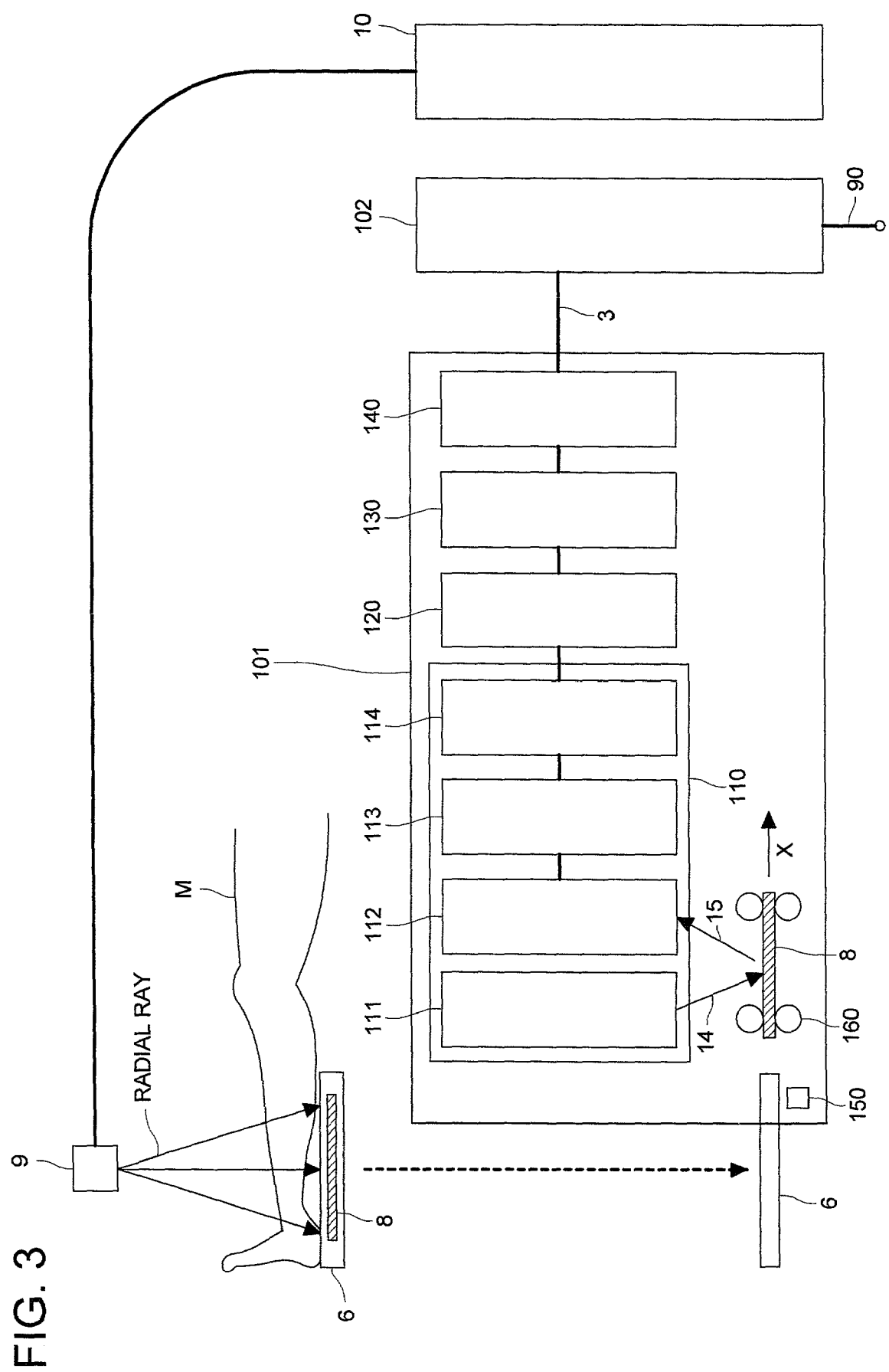
FIG. 3 shows a configuration of a radiation-image reading apparatus employed in the radiation-image radiographing system of the first embodiment of the present invention.
Figure 5:
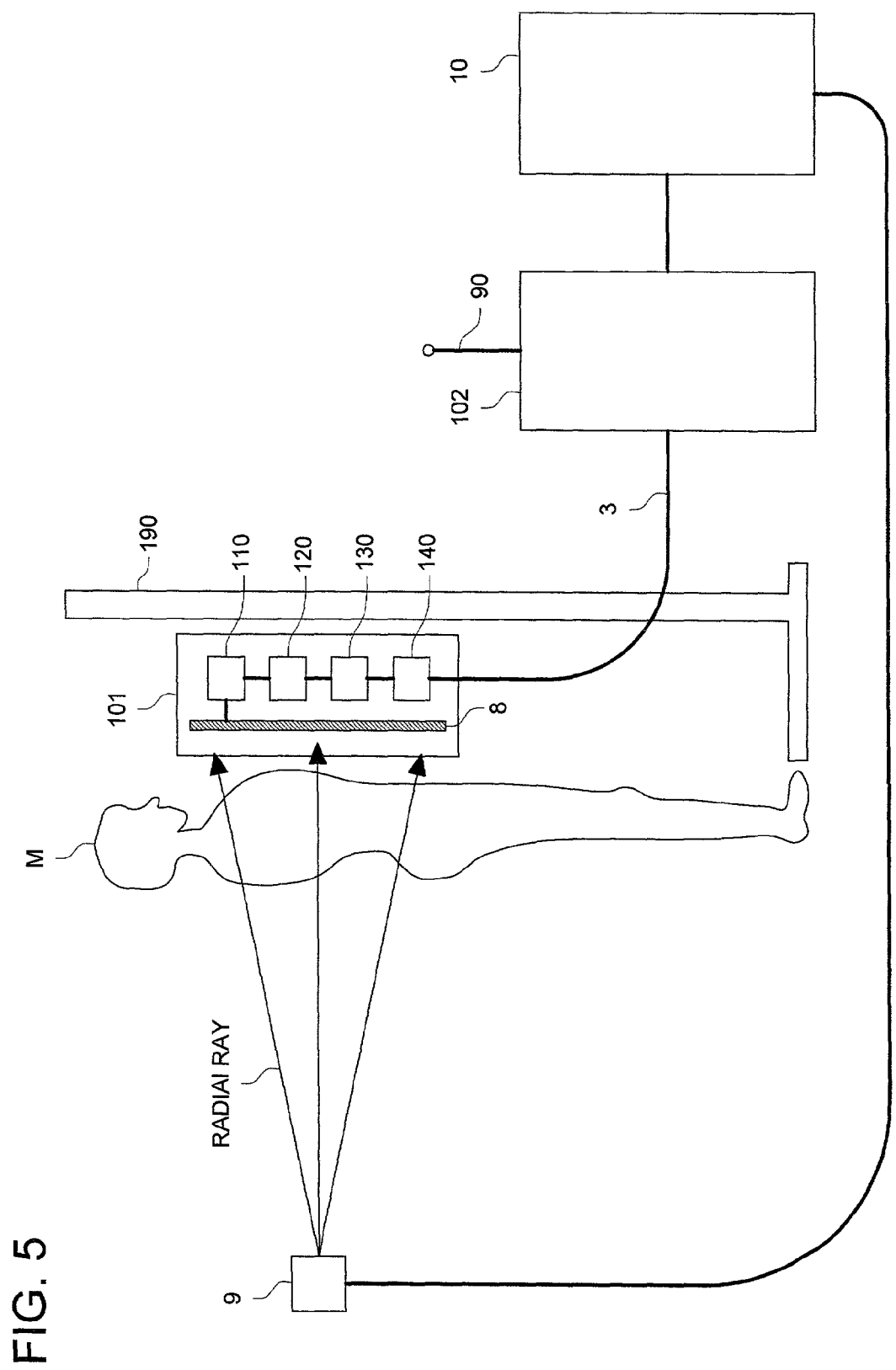
FIG. 5 shows a configuration of an exclusive-type (standing-type) radiation-image radiographing system of the fourth embodiment of the present invention.
Figure 6:
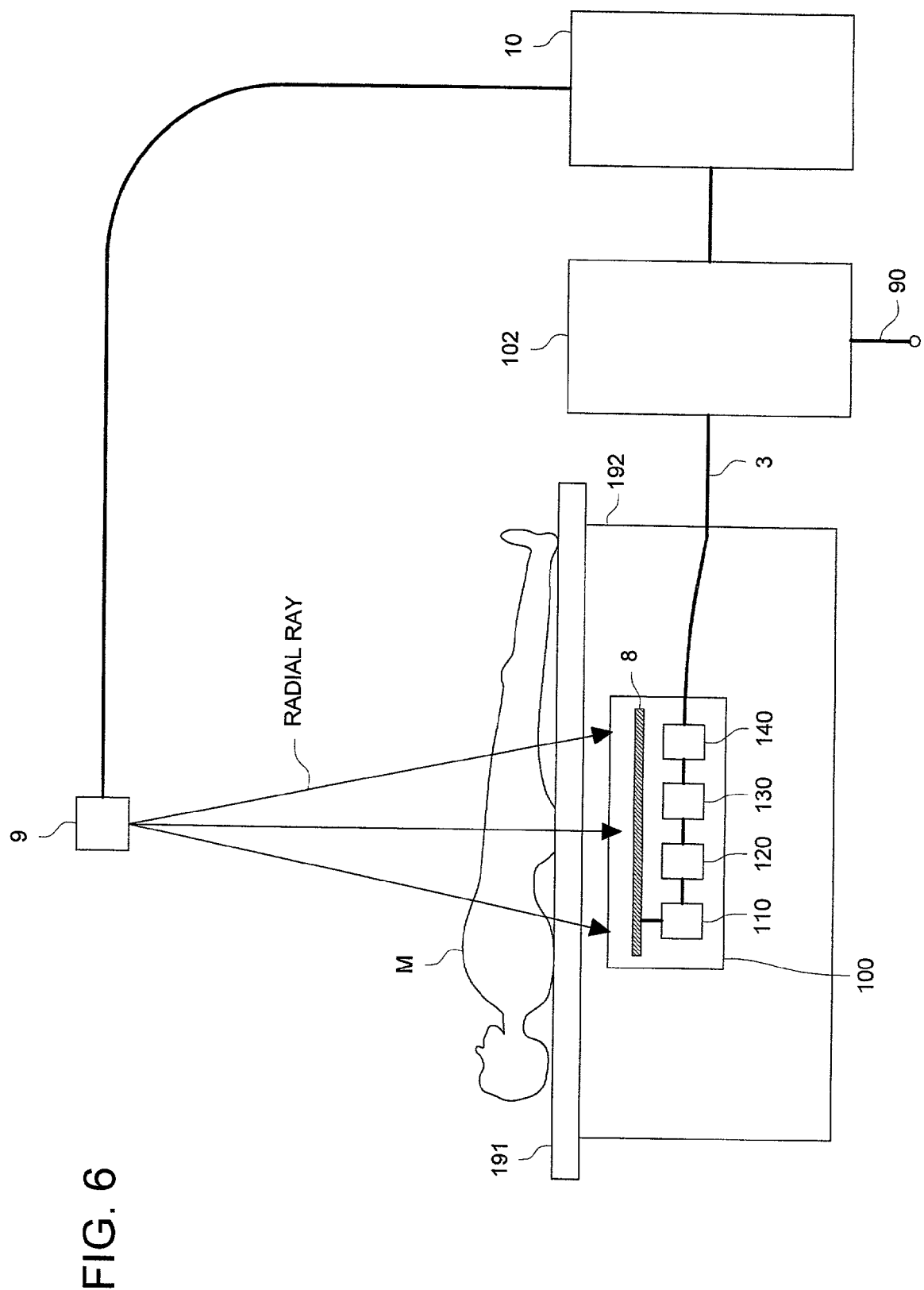
FIG. 6 shows a configuration of an exclusive-type (laying-type) radiation-image radiographing system of the fourth embodiment of the present invention.

Generally, in the radiation-image reading apparatus, besides the radiation-image reading apparatus 101 using the cassette 6 as shown in FIG. 3, (hereinafter, this type radiation-image reading apparatus is appropriately called the cassette type radiation-image reading apparatus), there are exclusive type radiation-image reading apparatus as shown in FIG. 5 and FIG. 6. The exclusive type radiation-image reading apparatus is the radiation-image reading apparatus in which the user can not simply carry the detection means because the detection means (detector section) detecting the X ray is fixed inside the radiographing apparatus or housed there. As the detection means, besides the stimulable phosphor substance sheet 8, the solid plane detector can also be used.

FIG. 5 shows a block diagram of the standing type radiographing system, which comprises a radiation-image reading apparatus 101A and an elevating stand 190 for rising up and falling down the radiation-image reading apparatus 101A.

FIG. 6 shows a block diagram of the laying type radiographing system, which comprises a radiation-image reading apparatus 101B, a plate-like member 191 and a bed 192.

The radiation-image reading apparatus 101A and the radiation-image reading apparatus 101B are respectively structured by a reading section 110, signal processing section 120, primary storing section 130, and communication section 140, and both of the function and movement are the same as the radiation-image reading apparatus 101 described in FIG. 3. Further, the inside of the reading section 110 is structured by the excitation light generating section, photoelectric reading section, and A/D converter (any one of them is not shown), and both of the function and movement are the same as the radiation-image reading apparatus 101 described in FIG. 3.

The different points of the radiation-image reading apparatus 101A and the radiation-image reading apparatus 101B from the radiation-image reading apparatus 101 are described in the following items (a)–(c).
(a) The reading out of the stimulable phosphor substance sheet 8 is started synchronized with the generation of the radiation from the radiation tube 9.
(b) For having this synchronization, the controller 102a, 2b conducts the communication relating to the synchronous signal of the radiation irradiation with the radiation generation control apparatus 10.
(b) The registration of the sheet ID number of the stimulable phosphor substance sheet 8 is not necessary.

Next, the movement in the case where the radiation-image reading apparatus 101A and the radiation-image reading apparatus 101B are used will be described.

After the radiologist registers the patient by the controller 102 (102a in FIG. 7), he sets the subject M at a predetermine position of the radiation-image reading apparatus 101A or the radiation-image reading apparatus 101B, and operates the radiation generation control apparatus 10 of the radiation tube 9 and irradiates the radiation. Then, a portion of the X ray energy, which is irradiated from the X ray tube 9 and penetrated the subject M, is stored once in the stimulable phosphor substance sheet 8 housed in the cassette 6.

Being synchronized with this radiation irradiation, the reading section 110 reads the image information from the stimulable phosphor substance sheet 8, and through the signal processing section 120, primary storing section 130, and communication section 140, the image data is transmitted to the controller 102a or 102b.

Till now, these exclusive type radiation-image reading apparatus and the cassette type radiation-image reading apparatus are controlled by individual controllers. However, when the exclusive type radiation-image reading apparatus and the cassette type radiation-image reading apparatus are arranged in the same radiographing room, because it is necessary that they are controlled by respectively different controllers, the disadvantage that the number of installations of the controller, installation area, installation cost are increased, is indicated. Further, when the same patient is photographed by the exclusive type radiation-image reading apparatus and the cassette type radiation-image reading apparatus, because it is necessary that the registration of the patient information and radiographing information, and the image confirmation are conducted by different controller, thereby, the operation efficiency is very lowered, and the operation mistake is increased.

In the embodiment of the present invention, in order to solve these problems, the exclusive type radiation-image reading apparatus 101A and 101B can be controlled by the cassette type controller 102.

Figure 7:
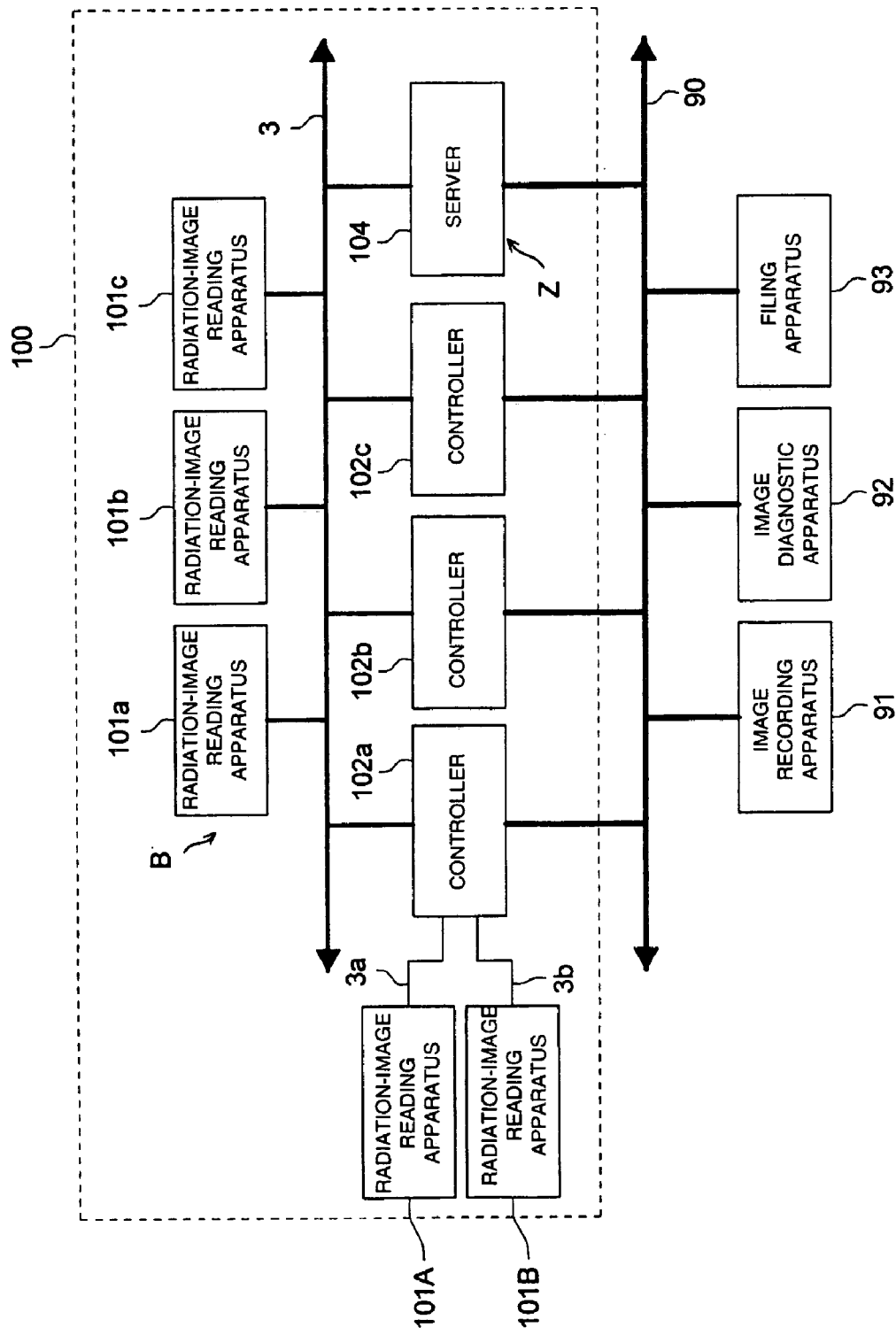
FIG. 7 shows another configuration of a radiation-image radiographing system, being a modified example of the first embodiment of the present invention.

FIG. 7 shows an example of the fourth embodiment, being the modified embodiment of the first, second and third embodiments mentioned above. The exclusive type radiation-image reading apparatus 101a and 1b are connected to the controller 102 shown by an arrow A, respectively through private lines 3a and 3b. The other controller 102b - - - can also connect the exclusive type radiation-image reading apparatus 101A and 101B in the same manner. In the present embodiment, the case is assumed that exclusive type radiation-image reading apparatus 101A and 101B, and the cassette type radiation-image reading apparatus 101a - - - shown by an arrow B, are installed in the same radiographing room, and the radiologist normally uses these radiation-image reading apparatus by the controller 102a shown by the arrow A. In this case, because the exclusive type radiation-image reading apparatus 101A and 101B are connected to the controller 102a shown by the arrow A through the private lines 3a and 3b, the image data transmitted from the exclusive type radiation-image reading apparatus 101A and 101B can be received only by the controller 102a shown by the arrow A. However, the controller 102a shown by the arrow A can receive the image data from not only the cassette type radiation-image reading apparatus 101a shown by the arrow B, but also from the other cassette type radiation-image reading apparatus 101b, 101c - - - .

Thereby, when the exclusive type radiation-image reading apparatus and the cassette type radiation-image reading apparatus are installed in the same radiographing room, it is not necessary that respectively different controllers control the apparatus, thereby, the number of installations of the controllers, installation area, and apparatus cost can be lowered. Further, when the same patient is photographed by the exclusive type radiation-image reading apparatus and the cassette type radiation-image reading apparatus, because the registration of the patient information, and radiographing information or the image confirmation can be conducted by the same controller, the operation efficiency is increased and the operation mistake can be reduced.

Fifth Embodiment

Figure 8:
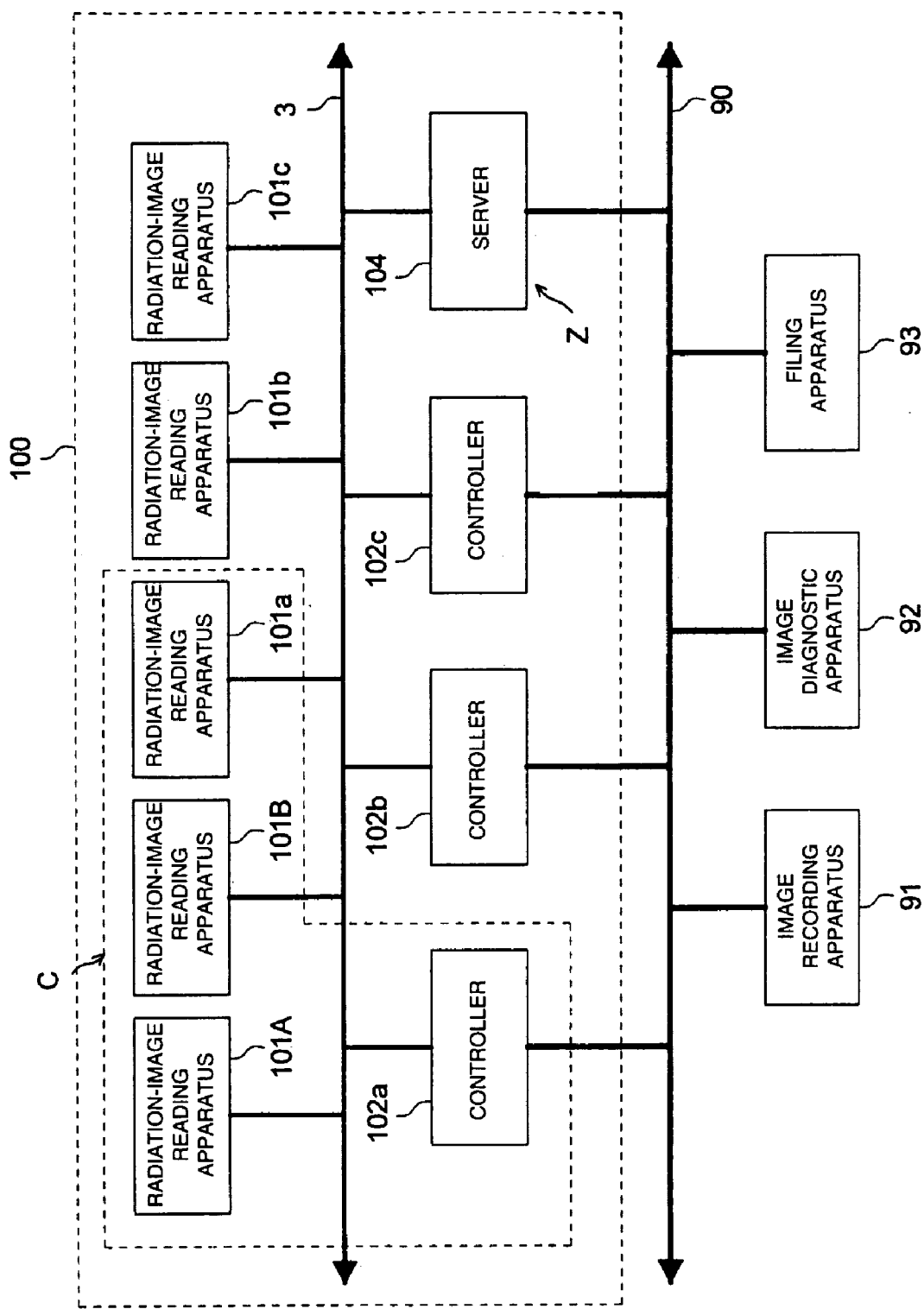
FIG. 8 shows still another configuration of a radiation-image radiographing system, being a modified example of the embodiment shown in FIG. 7.

FIG. 8 shows an example of the fifth embodiment, being a modified embodiment of the fourth embodiment shown in FIG. 7. In FIG. 8, the exclusive type radiation-image reading apparatus 101A and 101B are connected to arbitrary controllers 102a through network 3. Therefore, the arbitrary controller 102a can receive the image data from the exclusive type radiation-image reading apparatus 101A and 101B. A case in which the apparatus surrounded by dotted line shown by an arrow C are installed in one radiographing room, is assumed in FIG. 8.

When the exclusive type radiation-image reading apparatus 101A (standing-posture type) and 101B (laying-posture type) are used, the radiologist normally conducts the registration of the patient information and radiographing information, or image confirmation by the controller 102a shown by an arrow D, however, by any trouble, when the controller 102a can not receive the image data transmitted from the radiation-image reading apparatus 101A and 101B, the image data can be received by the other controller 102b, 102c, - - - . Accordingly, the high reliable system can be structured.

Sixth Embodiment

Figure 9:
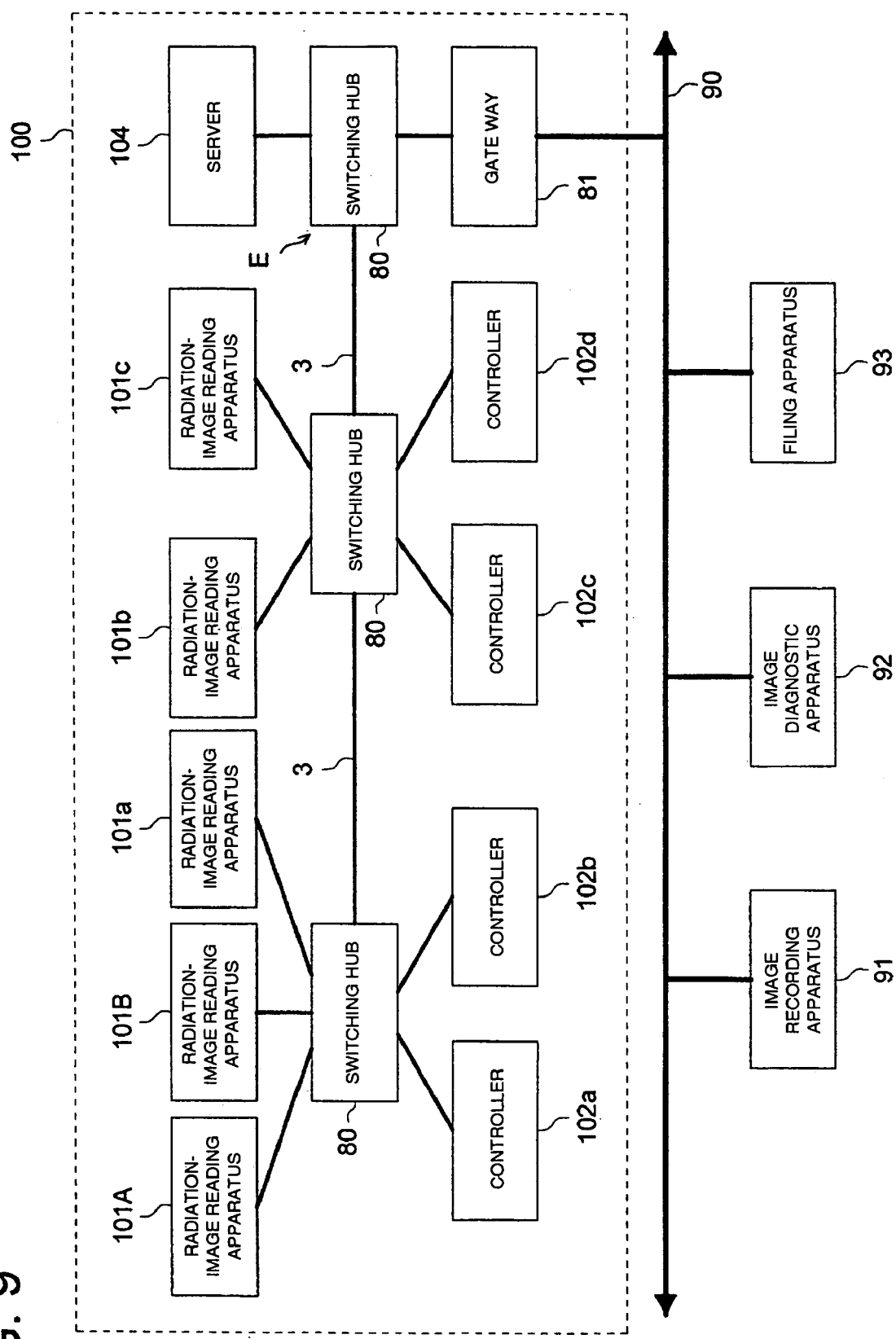
FIG. 9 shows still another configuration of a radiation-image radiographing system, being a modified example of the embodiment shown in FIG. 8.

FIG. 9 shows an example of the sixth embodiment, being a modified embodiment of the fifth embodiment shown in FIG. 8. In FIG. 9, the exclusive type radiation-image reading apparatus 101A, 101B and the cassette type radiation-image reading apparatus 101a - - - 101c or controllers 102a - - - 102d are connected by a switching hub 80.

The server 104 is connected to the switching hub shown by an arrow E, however, even when the server 104 does not exist, it is needless to say that the system can be operated without any problem as in the embodiments described above. The network 3 and the DICOM network 90 are connected by a gate way 81. The image data outputted by the controller 102 is outputted to the DICOM network 90 through the switching hub 80 and the gate way 81. In the sixth embodiment, because the exclusive type radiation-image reading apparatus 101A and 101B or cassette type radiation-image reading apparatus 101, or controller 102 are dispersedly connected by the switching hub 80, the image data transmission time when the image data transmission between the exclusive type radiation-image reading apparatus 101, 1a, 1b and the controller 102 is generated at the same time, is improved. Because a large quantity of image data flow on the network 3 connecting between switching hubs 80, it is preferable that the cable with large transmission capacity is used.

Seventh Embodiment

Figure 10:
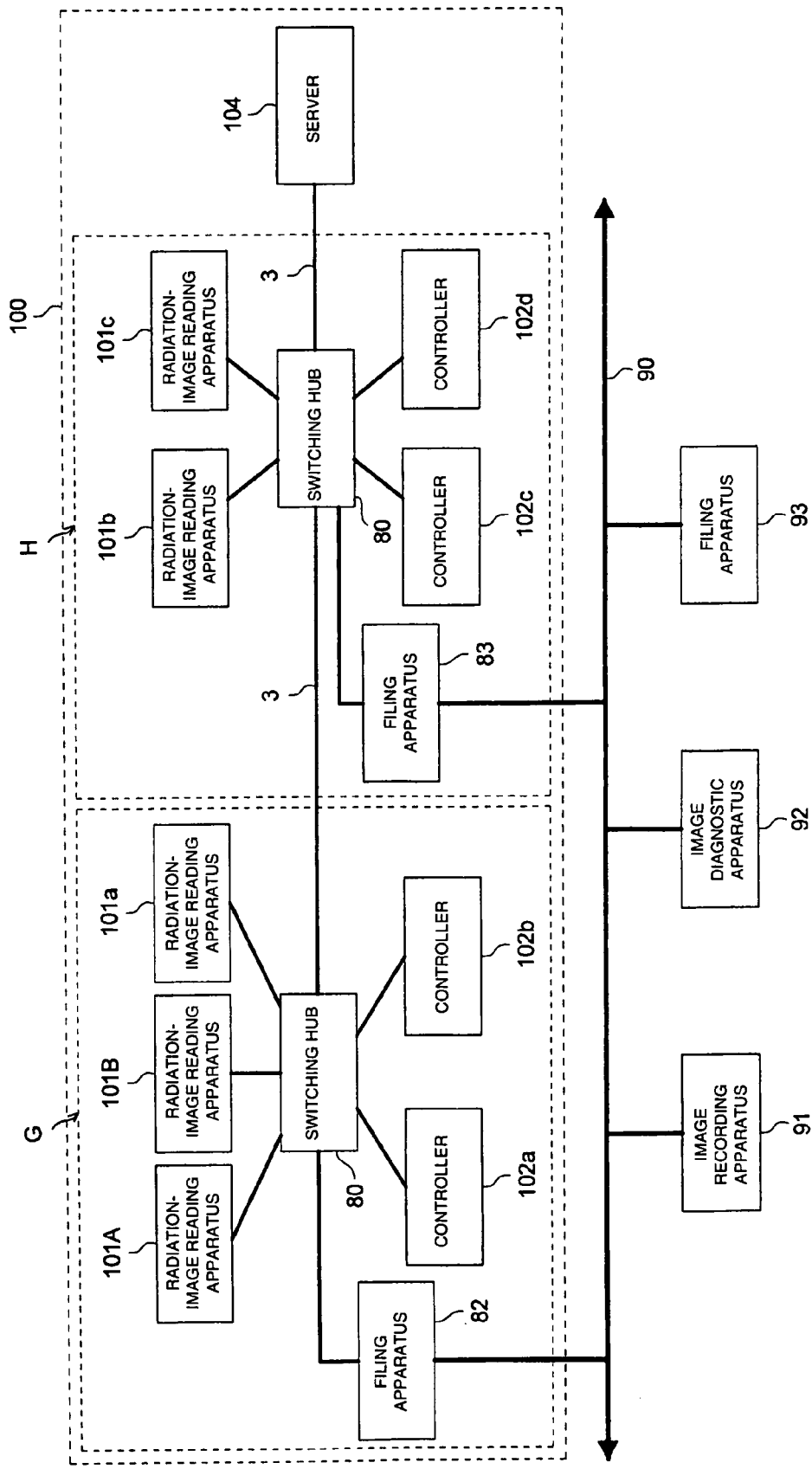
FIG. 10 shows still another configuration of a radiation-image radiographing system, being a modified example of the embodiment shown in FIG. 9.
Figure 11:
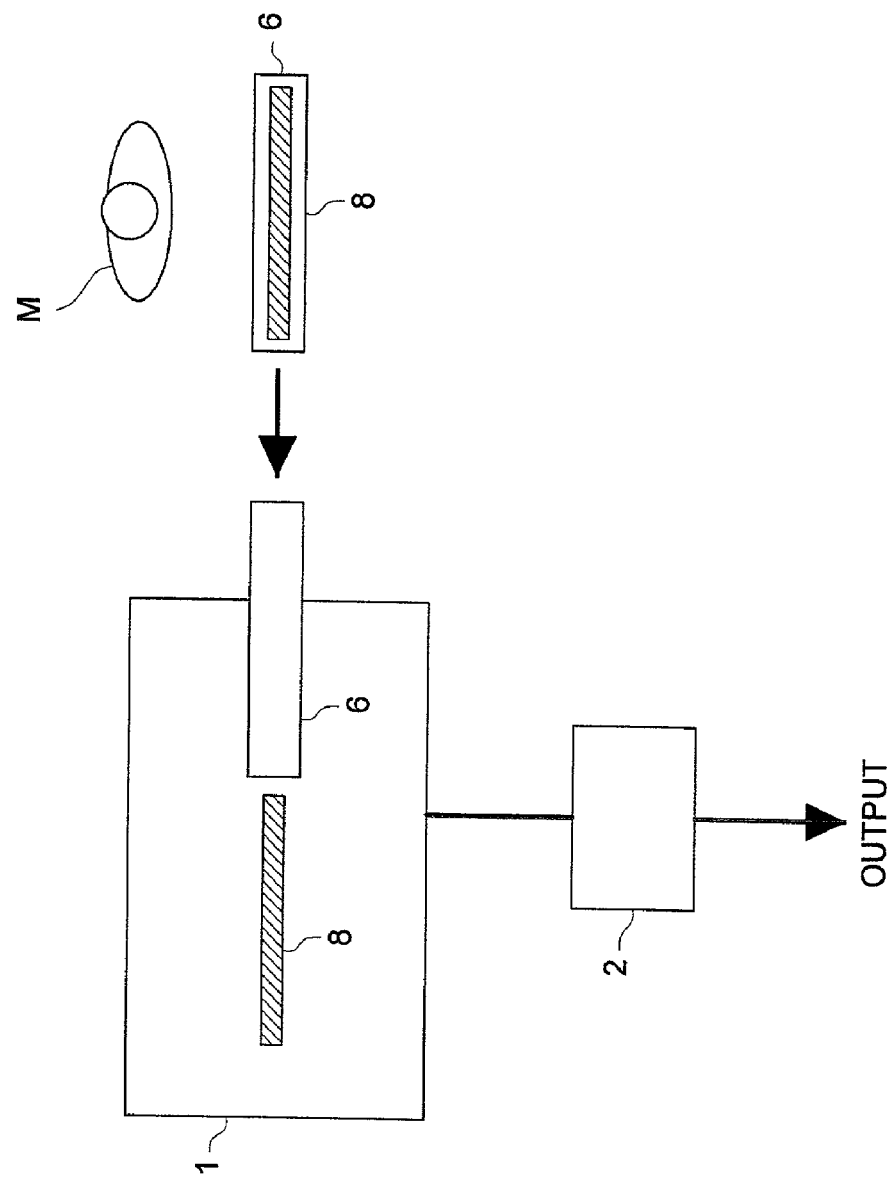
FIG. 11 shows an exemplified configuration of the conventional radiation-image radiographing system, being a cassette-type.
Figure 12:
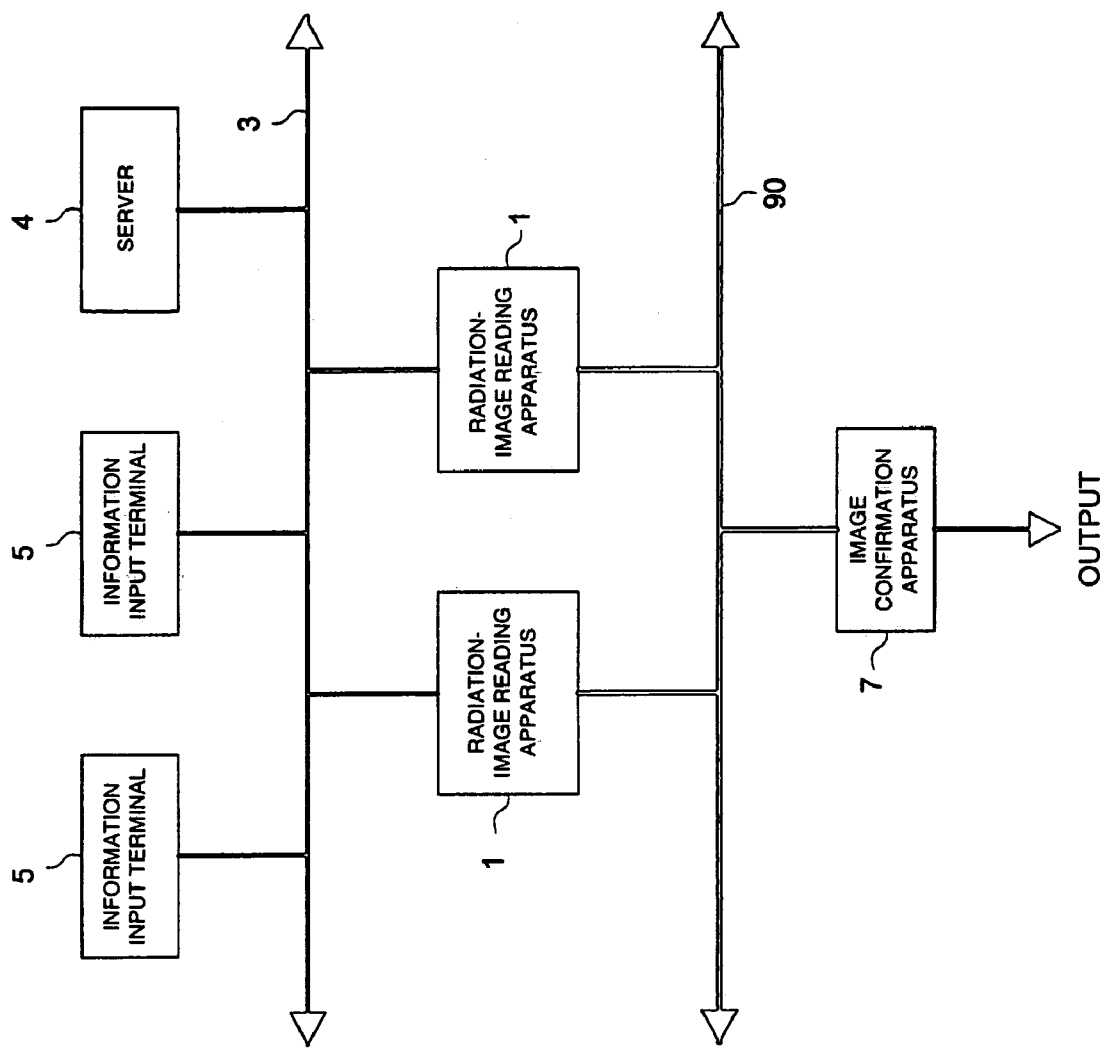
FIG. 12 shows another exemplified configuration of the conventional radiation-image radiographing system, being a cassette-type.

FIG. 10 shows an example of the seventh embodiment, being a modified embodiment of the sixth embodiment shown in FIG. 9. Local image filing apparatus 82 and 83 commonly used as the DICOM gate way, file the image data generated in portions respectively surrounded by arrows G and H. The server 104 is a server which controls the information generated in portions surrounded by dotted lines of arrows G and H, and even when this server 104 does not exist, it is needless to say that the system can be operated without any problem as in the embodiments described above. The database in the local image filing apparatus 82 and 83 are controlled by the image filing apparatus 93.

OTHER EMBODIMENT

To the DICOM network 90 described in the forth embodiment (refer to FIG. 7), the fifth embodiment (refer to FIG. 8), the sixth embodiment (refer to FIG. 9) and the seventh embodiment (refer to FIG. 9), the image recording apparatus 91 such as a laser imager and the image diagnostic apparatus 92 and the filing apparatus 93 and so on can be connected in the same manner as described in the first embodiment. The image recording apparatus 91 provides the visualized diagnostic image to the doctor, by outputting the image data, which is outputted from the controller 102, on the film, and the image diagnostic apparatus 92 provides the visualized diagnostic image to the doctor by displaying the image data outputted from the controller 102 on a monitor. The image filing apparatus 93 stores the image data outputted from the controller 102. The image data stored in the image filing apparatus 93 can be outputted at need to the image output apparatus 91 or the image diagnostic apparatus 92.

As described in the above, the following effects can be attained.

(1) Since the controller requests to transmit the image data to the controller concerned, even if the image data is read from a radiation-image storing sheet set in anyone of radiation-image reading apparatus designated by the controller concerned, and the radiation-image reading apparatus, which is requested to transmit the image data by the controller, transmits the image data of the radiation-image read from the radiation-image storing sheet to the controller, even when anyone of the plurality of radiation-image reading apparatus and the plurality of controllers malfunctions, the operation of the network system can be maintained by utilizing the other radiation-image reading apparatus and controllers being in normal conditions. Further, as a secondary effect, it is possible to prevent a specific radiographing room from being overloaded. Still further, the control mode of each of the controller side and the radiation-image reading apparatus side is advantageously simple, the development cost of the control software is low, and further, it is easily operated stably.

(2) Since the image data of the radiation-image read from the radiation-image storing sheet by the radiation-image reading apparatus are transmitted to all of the controllers arranged in the same network, even when anyone of the plurality of radiation-image reading apparatus and the plurality of controllers malfunctions, the operation of the network system can be maintained by utilizing the other radiation-image reading apparatus and controllers being in normal conditions. Further, as a secondary effect, it is possible to prevent a specific radiographing room from being overloaded. Still further, as its merits, the control mode of each of the controller side and the radiation-image reading apparatus side is the simplest, the development cost of the control software is low, and further, it is easily operated stably.

(3) Since the radiation-image reading apparatus transmits the discrimination information and the image data of the radiation-image read from the radiation-image storing sheet, and an operator-discrimination information with respect to the radiation-image to the server on the network, and the controller, which requests the image data, transmits the operator-discrimination information with respect to the radiation-image and the controller-information as a sending end of the image data to the server, and the server retrieves the requested discrimination information and the image data by using the operator-discrimination information as a retrieving-key, and then transmits the discrimination information and the image data to the controller serving as a sending end, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is possible to prevent a specific radiographing room from being overloaded.

(4) Since the radiation-image reading apparatus transmits the image data of the radiation-image read from the radiation-image storing sheet to a controller prioritized in advance as a sending end, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is possible to prevent a specific radiographing room from being overloaded.

(5) Since the radiation-image reading apparatus includes an operating means for setting a sending end, and transmits the discrimination information and the image data of the radiation-image read from the radiation-image storing sheet to the controller, which is set as the sending end in advance by the operating means, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is possible to prevent a specific radiographing room from being overloaded.

(6) Since the radiation-image reading apparatus includes a recording-medium handling means for recording the discrimination information and the image data into a recording medium while the controller includes a recording-medium handling means for reading the discrimination information and the image data stored in the recording medium, and since the discrimination information and the image data read from the radiation-image storing sheet by the radiation-image reading apparatus are transferred to the controller through the recording medium, even when anyone of the plurality of radiation-image reading apparatus and the plurality of controllers malfunctions, the operation of the network system can be maintained by utilizing the other radiation-image reading apparatus and controllers that are in normal conditions. Further, as a secondary effect, it is possible to prevent a specific radiographing room from being overloaded.

Disclosed embodiment can be varied by a skilled person without departing from the spirit and scope of the invention.

What is claimed is:

1. A radiographic imaging system, comprising:
a plurality of controllers, each of which is adapted to register a photographing order for a subject and to receive image data, and each of which includes an image-display section to display the received image data;
a plurality of radiation-image reading apparatuses, at least a plurality of which generate image data from respective radiation images stored in respective radiation-image storing mediums, in accordance with one said photographing order for a target patient from one of the controllers; and
a network to link the plurality of controllers and the plurality of radiation-image reading apparatuses to each other;
wherein the controller that has registered the one said photographing order for the target patient is specified, and each of the radiation-image reading apparatuses that have generated image data in accordance with the one said order transmit the generated image data of the target patient to the specified controller through the network so that the specified controller displays the image data of the target patient; and
wherein the plurality of controllers are prioritized in advance, and when the generated image data cannot be transmitted to the specified controller, the radiation-image reading apparatuses transmit the generated image data to a given one of the controllers having a highest priority among the controllers able to receive the image data among the plurality of controllers.

2. The radiographic imaging system of claim 1, wherein the controller that has registered the one said photographing order reads medium-discrimination information identifying the radiation-image storing mediums, and when the radiation-image reading apparatuses transmit the generated image data, each radiation image reading apparatus correlates, stores and transmits the image data and the medium-discrimination information read from the radiation-image storing medium.

3. The radiographic imaging system of claim 1, wherein each of the controllers is adapted to request one of the radiation-image reading apparatuses to transmit the image data thereto.

4. The radiographic imaging system of claim 1, wherein any of the plurality of radiation-image reading apparatuses is capable of reading the radiation-image storing mediums.

5. The radiographic imaging system of claim 1, wherein at least one of the radiation-image reading apparatuses is a standing- or laying-posture radiographing apparatus which is connected to the network and which includes one of the radiation-image storing mediums and reads the radiation image stored in the radiation-image storing medium so as to generate the image data.

6. The radiographic imaging system of claim 1,
wherein, when the image data cannot be transmitted to the controller having the highest priority degree, the radiation-image reading apparatuses transmit the image data to another one of the controllers having a next-highest priority degree among the plurality of controllers.

7. A radiographic imaging system, comprising:

a plurality of image data generating apparatus, each of which includes an image data generating section for generating image data representing a radiation image formed by radiation rays penetrated through a subject, an image data storing section for temporarily storing the image data generated by the image data generating section, and an image-data transmitting section for transmitting the image data which is read from the image data storing section;

a plurality of controllers, each of which includes an image data receiving section capable of receiving the image data transmitted by the image-data transmitting section, and an image display for displaying the radiation image based on the image data; and a network to link the plurality of image data generating apparatuses and the plurality of controllers to each other;

wherein one of the controllers registers a photographing order for a target patient, and at least a plurality of the image generating apparatuses generate image data in accordance with the photographing order, and wherein the one of the controllers is specified and each image data generating apparatus that has generated the image data in accordance with the photographing order sends the generated image data of the target patient to the specified controller through the network so that the specified controller displays the image data of the target patient;

wherein a priority degree is attached to each of the plurality of controllers according to a priority order of the plurality of controllers, and when the generated image data cannot be transmitted to the specified controller, the image data generating apparatuses transmit the image data to a given one of the controllers having a highest priority degree among the plurality of controllers; and wherein, when the image data cannot be transmitted to the controller having the highest priority degree, the image data generating apparatuses transmit the image data to another one of the controllers having a next-highest priority degree among the plurality of controllers.

8. A radiographic imaging system, comprising:

a plurality of controllers, each of which is adapted to register a photographing order for a subject and to receive image data, and each of which includes an image-display section to display the received image data;

a plurality of radiation-image data generating apparatuses, at least a plurality of which generate image data from respective radiation images stored in respective radiation-image storing mediums in accordance with one said photographing order for a target patient from one of the controllers; and a network to link the plurality of controllers and the plurality of radiation-image data generating apparatuses to each other;

wherein the controller that has registered the one said photographing order for the target patient is specified, and the plurality of controllers are prioritized in advance; and wherein each of the radiation-image data generating apparatuses transmits the image data of the target patient generated from the stored radiation image to both: (i) the specified controller through the network so that the specified controller displays the image data of the target patient, and (ii) a given one of the controllers having a highest priority among the controllers able to receive the image data among the plurality of controllers.

* * * * *